United States Patent [19]

Nyffeler et al.

[11] Patent Number: 4,881,966
[45] Date of Patent: Nov. 21, 1989

[54] USE OF QUINOLINE DERIVATIVES FOR THE PROTECTION OF CULTIVATED PLANTS

[75] Inventors: Andreas Nyffeler; Adolf Hubele, both of Maden, Switzerland

[73] Assignee: Ciba-Geigy Corporation, Ardsley, N.Y.

[21] Appl. No.: 178,805

[22] Filed: Mar. 30, 1988

Related U.S. Application Data

[63] Continuation of Ser. No. 829,600, Feb. 13, 1986, abandoned.

[30] Foreign Application Priority Data

Feb. 14, 1985 [CH] Switzerland ............................ 682/85
Dec. 2, 1985 [CH] Switzerland ........................ 5132/85

[51] Int. Cl.⁴ ............................................. A01N 43/42
[52] U.S. Cl. ............................................ 71/94; 71/88; 71/90; 71/92; 546/176; 546/177
[58] Field of Search ....................................... 71/94, 88

[56] References Cited

U.S. PATENT DOCUMENTS 4,505,743  3/1985  Shurter et al. ........................... 71/94
4,531,969  7/1985  Nestler et al. ........................... 71/94
4,602,932  7/1986  Handte et al. ........................... 71/94

FOREIGN PATENT DOCUMENTS 83556   11/1983  European Pat. Off. .
0094349 11/1983  European Pat. Off. ................. 71/94
97460    1/1984  European Pat. Off. .
86750    3/1984
0159287 10/1985  European Pat. Off. ................. 71/94
0159290 10/1985  European Pat. Off. .
2546845  4/1977  Fed. Rep. of Germany .

OTHER PUBLICATIONS

"Composite List of Weeds", Journal of the Weeds Science Society of America, Vol. 32 (1984).
Grass Weeds 2, edited by E. Hafliger et al.
The New Encyclopaedia Britannica in vol. 30, vol. 3, Cereals and Other Starch Products–pp. 1157–1167.
"The Pesticide Manual, A World Compendium", 8th edition, C. R. Worthing, editor, p. 379.

Primary Examiner—Glennon H. Hollrah
Assistant Examiner—Amelia A. Owens
Attorney, Agent, or Firm—Edward McC. Roberts

[57] ABSTRACT

The use of quinoline derivatives of the formula

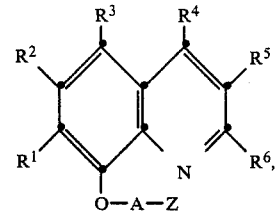

against the harmful effects of herbicidally active 2-[4-(5-chloro-3-fluoropyridin-2-yloxy)-phenoxy]-propionic acid derivatives.

8 Claims, No Drawings

USE OF QUINOLINE DERIVATIVES FOR THE PROTECTION OF CULTIVATED PLANTS

This application is a continuation of application Ser. No. 829,600, filed Feb. 13, 1986, now abandoned.

The present invention relates to the use of quinoline derivatives for the protection of cultivated plants against the harmful effects of herbicidally active 2-[4-(5-chloro-3-fluoropyridin-2-yloxy)-phenoxy]-propionic acid derivatives, and to herbicidal compositions containing a combination of herbicide and a protecting quinoline derivative. The invention relates also to novel quinoline derivatives.

With the use of herbicides, such as with the use of the aforementioned propionic acid derivatives, the cultivated plants can to a considerable extent suffer damage, depending on such factors as for example the dosage of the herbicide used and the mode of application, variety or type of cultivated plant, nature of the soil and climatic conditions, for example: duration of exposure to light, temperature and rainfall. Severe damage can occur in particular when, in the course of crop rotation, the cropping of cultvated plants resistant to the herbicides is followed by the cultivation of other cultivated plants which have no resistance, or inadequate resistance, to the herbicides that have been used.

It is known from the European Patent Publication Nos. 86,750 and 94,349 that quinoline derivatives can be used to protect cultivated plants against the harmful effects of aggressive agricultural chemicals.

It has now been found that, surprisingly, a protection of cultivated plants against damage otherwised caused by herbicidally active 2-[4-(5-chloro-3-fluoropyridin-2-yloxy)phenoxy]-propionic acid derivatives can be provided by treatment of the cultivated plants or parts of these plants, or of soils intended for the cultivation of the cultivated plants, with a safener (antidote) selected from a group of quinoline derivatives. The herbicidal action against weeds and wild grasses is not rendered ineffective by the quinoline derivatives.

Quinoline derivatives which are suitable for protecting cultivated plants aganst the harmful effects of herbicidally active 2-[4-(5-fluoropyridin-2-yloxy)-phenoxy]-propionic acid derivatives correspond to the formula I

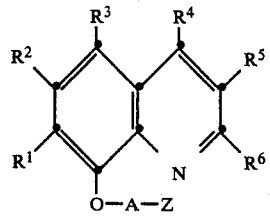

(I)

wherein $R^1$, $R^2$ and $R^3$ independently of one another are each hydrogen, halogen, nitro, cyano, $C_1$-$C_3$-alkyl or $C_1$-$C_3$-alkoxy, $R^4$, $R^5$ and $R^6$ independently of one another are each hydrogen, halogen or $C_1$-$C_3$-alkyl, A is any one of the groups —$CH_2$—, —$CH_2$—$CH_2$— or —$CH(CH_3)$—, and Z (a) is cyano or amidoxime, which can be acylated on the oxygen atom, or (b) is a carboxyl group or a salt thereof, a mercaptocarbonyl group or a salt thereof, a carboxylic acid ester group, a carboxylic acid thiol ester group, an unsubstituted or substituted carboxylic acid amide group, a cyclised, unsubstituted or substituted derivative of a carboxylic acid amide group, or a carboxylic acid hydrazide group, or A and Z together form an unsubstituted or substituted tetrahydrofuran-2-one ring;
with the inclusion of the acid addition salts and metal complexes thereof.

By amidoxime is meant the group —$C(NH_2)$=N—OH. The amidoxime can be acylated on the oxygen atom. Amidoximes acylated on the oxygen atom are those of the formula —$C(NH_2)$=N—O—CO—E, in which E is —$R^7$, —$OR^8$, —$SR^9$ or —$NR^{10}R^{11}$, wherein $R^7$ is $C_1$-$C_7$-alkyl, unsubstituted or substituted by halogen or $C_1$-$C_4$-alkoxy, or is $C_3$-$C_6$-cycloalkyl, $C_2$-$C_4$-alkenyl, phenyl which is unsubstituted or substituted by halogen, nitro or $C_1$-$C_3$-alkyl, benzyl which is unsubstituted or substituted by halogen, nitro or $C_1$-$C_3$-alkyl, or is a 5- or 6-membered heterocyclic ring which contains one or two hetero atoms from the group N, O and S, and which is unsubstituted or substituted by halogen; $R^8$, $R^9$ and $R^{10}$ independently of one another are each $C_1$-$C_8$-alkyl which is unsubstituted or substituted by halogen, or are $C_2$-$C_4$-alkenyl, $C_3$-$C_6$-alkynyl, phenyl which is unsubstituted or substituted by halogen, $C_1$-$C_3$-alkyl, $C_1$-$C_3$-alkoxy, trifluoromethyl or nitro, or are benzyl which is unsubstituted or substituted by halogen or nitro; $R^{11}$ is hydrogen, $C_1$-$C_8$-alkyl or $C_1$-$C_3$-alkoxy, or $R^{10}$ and $R^{11}$ together with the nitrogen atom to which they are bound are a 5- or 6-membered heterocycle that can contain a further hetero atom from the group N, O and S.

Heterocycles denoted by $R^8$ can be saturated, partially saturated or unsaturated heterocycles, for example thiophene, furan, tetrahydrofuran and pyrimidine.

Heterocycles formed by $R^{10}$ and $R^{11}$ together with the nitrogen atom to which they are linked are saturated, partially saturated or unsaturated heterocycles. Examples of such heterocycles are: pyrrolidine, pyrroline, pyrrole, imidazolidine, imidazoline, imidazole, piperazine, pyridine, pyrimidine, pyrazine, thiazine, oxazole, thiazole and, in particular, piperidine and morpholine.

Alkyl as constituent of the acylated amidoxime Z embraces, within the limits of the stated number of carbon atoms, all straight-chain and all branched chain alkyl groups.

$C_3$-$C_6$-Cycloalkyl denoted by $R^7$ is cyclopropyl, cyclobutyl, cyclopentyl or cyclohexyl.

To be mentioned among the $C_2$-$C_4$-alkenyl or $C_3$-$C_6$-alkynyl groups, as constituents of the acylated amidoxime Z, are in particular: vinyl, allyl, 1-propenyl, methallyl and propargyl.

Applicable for Z as a carboxylic acid ester group or a carboxylic acid thiol ester group is a corresponding acid radical which is esterified for example by an unsubstituted or substituted aliphatic radical, or by a cycloaliphatic, aromatic or heterocyclic radical which is optionally bound by way of an aliphatic radical and which is unsubstituted or substituted.

A preferred carboxylic acid ester radical is the radical —$COOR^{12}$ and a preferred carboxylic acid thiol ester radical is the radical —$COSR^{13}$, wherein $R^{12}$ and $R^{13}$ have the following meanings: an unsubstituted or substituted alkyl, alkenyl, alkynyl, cycloalkyl, phenyl or naphthyl radical or an unsubstituted or substituted heterocyclic radical. The radicals —$COOR^{12}$ and —COSR$^{13}$ also include the free acids, R$^{12}$ and R$^{13}$ being hydrogen, and also the salts thereof, R$^{12}$ and R$^{13}$ then being a cation. Suitable salt formers are in this case particularly metals and organic nitrogen bases, especially quaternary ammonium bases. Metals suitable for salt formation are alkaline-earth metals, such as magnesium or calcium, in particular however the alkali metals, such as lithium and especially potassium and sodium. Also suitable as salt formers are transition metals, for example iron, nickel, cobalt, copper, zinc, chromium and manganese. Examples of nitrogen bases suitable for forming salts are: primary, secondary or tertiary, aliphatic and aromatic amines which are optionally hydroxylated on the hydrocarbon radical, such as methylamine, ethylamine, propylamine, isopropylamine, the four isomeric butylamines, dimethylamine, diethylamine, dipropylamine, diisopropylamine, di-n-butylamine, pyrrolidine, piperidine, morpholine, trimethylamine, triethylamine, tripropylamine, quinuclidine, pyridine, quinoline and isoquinoline, as well as methanolamine, ethanolamine, propanolamine, dimethanolamine, diethanolamine and triethanolamine. Suitable nitrogen bases are also quaternary ammonium bases. Examples of quaternary ammonium bases are tetraalkylammonium cations in which the alkyl radicals independently of one another are straight-chain or branched-chain $C_1$–$C_6$-alkyl groups, such as the tetramethylammonium cation, the tetraethylammonium cation or the trimethylethylammonium cation, and also the trimethylbenzylammonium cation, the triethylbenzylammonium cation and the trimethyl-2-hydroxyethylammonium cation. Particularly preferred salt formers are the ammonium cation and trialkylammonium cations, in which the alkyl radicals independently of one another are straight-chain or branched-chain $C_1$–$C_6$-alkyl groups, especially $C_1$–$C_2$-alkyl groups, which are unsubstituted or substituted by a hydroxyl group, for example the trimethylammonium cation, the triethylammonium cation and the tri-(2-hydroxyethylene)-ammonium cation.

A carboxylic acid amide group denoted by Z is a corresponding amide radical which is unsubstituted or can be mono- or disubstituted on the nitrogen atom, or in which the nitrogen atom is a constituent of an unsubstituted or substituted heterocyclic radical. Substituents of the amide group are for example an unsubstituted or substituted aliphatic radical which is optionally bound by way of an oxygen atom, an unsubstituted or substituted cycloaliphatic, aromatic or heterocyclic radical which is optionally bound by way of an aliphatic radical, or an unsubstituted or mono- or disubstituted amino group.

A preferred carboxylic acid amide radical is the radical —CONR$^{14}$R$^{15}$, wherein R$^{14}$ is hydrogen, an unsubstituted or substituted alkyl, alkenyl, alkynyl, cycloalkyl, phenyl or naphthyl radical, an unsubstituted or substituted heterocyclic radical or an alkoxy radical, R$^{15}$ is hydrogen, amino, mono- or disubstituted amino or an unsubstituted or substituted alkyl, alkenyl, cycloalkyl or phenyl radical, or R$^{14}$ and R$^{15}$ together with the nitrogen atom to which they are linked form an unsubstituted or substituted heterocyclic radical.

Substituents of the organic radicals R$^{12}$, R$^{13}$, R$^{14}$ and R$^{15}$ are for example halogen, nitro, cyano, hydroxyl, alkyl, haloalkyl, alkoxy, which can be interrupted by one or more oxygen atoms, alkylthio, haloalkoxy, hydroxyalkoxy, which can be interrupted by one or more oxygen atoms, hydroxyalkylthio, alkoxycarbonyl, amino, alkylamino, dialkylamino, hydroxyalkylamino, di-(hydroxyalkyl)-amino, aminoalkylamino, cycloalkyl, unsubstituted or substituted phenyl, unsubstituted or substituted phenoxy or an unsubstituted or substituted heterocyclic radical.

By heterocyclic radicals as constituents of the carboxylic acid ester radical, of the carboxylic acid thiol ester radical and of the carboxylic acid amide radical are meant in particular 5- or 6-membered, saturated or unsaturated, unsubstituted or substituted monocyclic heterocycles having 1 to 3 hetero atoms from the group N, O and S, for example furan, tetrahydrofuran, tetrahydropyrane, tetrahydropyrimidine, pyridine, piperidine, morpholine and imidazole.

Cycloalkyl radicals as constituents of the carboxylic acid ester radicals, of the carboxylic acid thiol ester radical and of the carboxylic acid amide radical are especially those having 3 to 8, in particular 3 to 6, carbon atoms.

Aliphatic acyclic radicals present in the substituent Z as constituents of the carboxylic acid ester radical, of the carboxylic acid thiol ester radical and of the carboxylic acid amide radical can be straight-chain or branched-chain and advantageously contain up to a maximum of 18 carbon atoms. A smaller number of carbon atoms is frequently of advantage, especially in the case of combined substituents.

A cyclised derivative of a carboxylic acid amide group denoted by Z is in particular an unsubstituted or substituted oxazolin-2-yl radical, preferably an unsubstituted oxazolin-2-yl radical.

A and Z together can form an unsubstituted or substituted tetrahydrofuran-2-one ring, the unsubstituted tetrahydrofuran-2-one ring being preferred, especially the unsubstituted tetrahydrofuran-2-on-3-yl ring.

In the compounds of the formula I, halogen is fluorine, chlorine, bromine and iodine, particularly chlorine, bromine and iodine.

Salt formers for acid addition salts are organic and inorganic acids. Examples of organic acids are acetic acid, trichloroacetic acid, oxalic acid, benzensulfonic acid and methanesulfonic acid. Examples of inorganic acids are hydrochloric acid, hydrobromic acid, hydriodic acid, sulfuric acid, phosphoric acid, phosphorous acid and nitric acid.

Suitable metal-complex former are for example elements of the 3rd and 4th main group, such as aluminium, tin and lead, and also of the 1st to 8th subgroup, for example: chromium, manganese, iron, cobalt, nickel, zirconium, zinc, copper, silver and mercury. The subgroup elements of the 4th period are preferred.

When in the compounds of the formula I A is —CH(CH$_3$)— and the radical Z contains an asymmetrical carbon atom, or A and Z together form a tetrahydrofuran-2-one ring, there exist optically isomeric compounds. Within the scope of the present invention, there are meant by the corresponding compounds of the formula I both the optically pure isomers and the isomeric mixtures.

Where the structure is not more precisely given with the presence of one or more asymmetrical carbon atoms, the isomeric mixture is always to be understood.

Particularly suitable for application according to the invention are compounds of the formula I in which R$^1$, R$^2$ R$^4$, R$^5$ and R$^6$ are hydrogen, R$^3$ is hydrogen or chlorine, and the radical —A—Z is a group —CH$_2$—COOR$^{16}$ or —CH(CH$_3$)—COOR$^{16}$, wherein R$^{16}$ is $C_1$–$C_{12}$-alkyl, $C_3$–$C_6$-alkenyl, phenyl-$C_1$–$C_4$-alkyl or phenoxy-$C_1$–$C_4$-alkyl.

The following are listed as preferred individual compounds of the formula I for use according to the present invention:
2-quinolin-8-yloxy-acetic acid isopropyl ester,
2-(5-chloroquinolin-8-yloxy)-acetic acid-n-dodecyl ester,
2-(5-chloroquinolin-8-yloxy)-acetic acid-n-butyl ester,
2-(5-chloroquinolin-8-yloxy)-acetic acid-n-octyl ester,
2-quinolin-8-yloxy-acetic acid-s-butyl ester,
2-(5-chloroquinolin-8-yloxy)-thioacetic acid-n-octyl ester,
2-(5-chloroquinolin-8-yloxy)-acetic acid-(2-butenyl) ester,
2-(5-chloroquinolin-8-yloxy)-acetic acid methallyl ester,
2-(5-chloroquinolin-8-yloxy)-acetic acid-(2-isopropyloxyethyl) ester,
2-(5-chloroquinolin-8-yloxy)-acetic acid-(2-phenoxyethyl) ester,
2-(5-chloroquinolin-8-yloxy)-acetic acid-(1-methylbutyl) ester,
2-(5-chloroquinolin-8-yloxy)-acetic acid cyclohexyl ester,
2-(5-chloroquinolin-8-yloxy)-acetic acid-s-butyl ester,
2-(5-chloroquinolin-8-yloxy)-acetic acid-(2-methylpentyl) ester,
2-(5-chloroquinolin-8-yloxy)-thioacetic acid-n-butyl ester,
2-(5-chloroquinolin-8-yloxy)-acetic acid-(3,6-dioxadecyl) ester,
2-(5-chloroquinolin-8-yloxy)-acetic acid-(3-methoxybutyl) ester,
2-(5-chloroquinolin-8-yloxy)-acetic acid-(1-ethylbutyl) ester,
2-(5-chloroquinolin-8-yloxy)-acetic acid-(2-ethylbutyl) ester,
2-(5-chloroquinolin-8-yloxy)-acetic acid-(1-methylisopentyl ester,
2-(5-chloroquinolin-8-yloxy)-acetic acid-n-undecyl ester,
2-(5-chloroquinolin-8-yloxy)-acetic acid-(2-methylbutyl) ester,
2-(5-chloroquinolin-8-yloxy)-thioacetic acid-s-butyl ester,
2-(5-chloroquinolin-8-yloxy)-acetic acid-(3,6-dioxaheptyl) ester,
2-(5-chloroquinolin-8-yloxy)-acetic acid-n-heptyl ester,
2-(5-chloroquinolin-8-yloxy)-thioacetic acid-n-dodecyl ester,
2-(5-chloroquinolin-8-yloxy)-thioacetic acid-n-decyl ester,
2-(5-chloroquinolin-8-yloxy)-acetic acid-(1-propylpropargyl) ester,
2-(5-chloroquinolin-8-yloxy)-acetic acid-(1-methylisobutyl) ester,
2-(5-chloroquinolin-8-yloxy)-thioacetic acid-tert-butyl ester,
2-(5-chloroquinolin-8-yloxy)-acetic acid-neopentyl ester,
2-(5-chloroquinolin-8-yloxy)-thioacetic acid-n-propyl ester,
2-(5-chloroquinolin-8-yloxy)-acetic acid-(1-methylhexyl) ester,
2-(5-chloroquinolin-8-yloxy)-thioacetic acid ethyl ester,
2-(5-chloroquinolin-8-yloxy)-acetic acid-(2-ethylhexyl) ester,
2-(5-chloroquinolin-8-yloxy)-thioacetic acid-i-butyl ester,
2-quinolin-8-yloxy-thioacetic acid-n-decyl ester,
2-(5-chloroquinolin-8-yloxy)-acetic acid-i-pentyl ester,
2-(5-chloroquinolin-8-yloxy)-acetic acid-(1-ethylpentyl) ester,
2-(5-chloroquinolin-8-yloxy)-acetic acid-(1-propylbutyl) ester,
2-(5-chloroquinolin-8-yloxy)-thioacetic acid-n-hexyl ester,
2-(5-chloroquinolin-8-yloxy)-acetic acid-n-hexyl ester,
2-(5-chloroquinolin-8-yloxy)-thioacetic acid-i-propyl ester,
2-(5-chloroquinolin-8-yloxy)-acetic acid-(1-pentylallyl) ester,
2-(5-chloroquinolin-8-yloxy)-acetic acid-(1-methylpentyl) ester,
2-(5-chloroquinolin-8-yloxy)-acetic acid-(1,1-dimethylpropargyl) ester,
2-(5-chloroquinolin-8-yloxy)-acetic acid-(1-ethyl-1-methylpropargyl) ester,
2-(5-chloroquinolin-8-yloxy)-acetic acid-n-butyloxycarbonylmethyl ester,
2-(5-chloroquinolin-8-yloxy)-acetic acid-(1-n-butyloxycarbonylethyl) ester,
2-(5-chloroquinolin-8-yloxy)-acetic acid-(1-methylisohexyl) ester,
2-(5-chloroquinolin-8-yloxy)-acetic acid-(1-phenylisobutyl) ester,
2-(5-chloroquinolin-8-yloxy)-acetic acid-[1-methyl-2-(2-methylphenoxy)-ethyl]ester,
2-(5-chloroquinolin-8-yloxy)-acetic acid-(1-phenylethyl) ester,
2-(5-chloroquinolin-8-yloxy)-acetic acid-[1-methyl-2-(4-ethylphenoxy)-ethyl]ester,
2-(5-chloroquinolin-8-yloxy)-acetic acid-(1-methyl-2-phenylethyl) ester,
2-(5-chloroquinolin-8-yloxy)-acetic acid-[1-methyl-2-(2-isopropylphenoxy)-ethyl] ester,
2-(5-chloroquinolin-8-yloxy)-acetic acid-(1-phenylpropyl) ester,
2-(5-chloroquinolin-8-yloxy)-acetic acid-[1-methyl-2-(2-ethylphenoxy)-ethyl] ester,
2-(5-chloroquinolin-8-yloxy)-acetic acid-[1-methyl-2-(3-ethylphenoxy)-ethyl] ester,
2-(5-chloroquinolin-8-yloxy)-acetic acid-(1-methyl-2-phenoxyethyl) ester,
2-(5-chloroquinolin-8-yloxy)-acetic acid-(1-methyl-3-phenylpropyl) ester,
2-(5-chloroquinolin-8-yloxy)-acetic acid-[1-methyl-2-(3-methylphenoxy)-ethyl] ester,
2-(5-chloroquinolin-8-yloxy)-acetic acid-[1-methyl-2-(4-isopropylphenoxy)-ethyl] ester, and
2-(5-chloroquinolin-8-yloxy)-acetic acid-[1-methyl-2-(4-methylphenoxy)-ethyl] ester.

To be emphasised within the scope of the present invention is in particular the use of:
2-(5-chloroquinolin-8-yloxy)-acetic acid methallyl ester,
2-(5-chloroquinolin-8-yloxy)-acetic acid-(2-phenoxyethyl) ester,
2-(5-chloroquinolin-8-yloxy)-acetic acid-(1-methylbutyl) ester,
2-(5-chloroquinolin-8-yloxy)-acetic acid-(1-ethylbutyl) ester,
2-(5-chloroquinolin-8-yloxy)-acetic acid-(1-methylisopentyl) ester,
2-(5-chloroquinolin-8-yloxy)-acetic acid-(1-methylhexyl) ester, 2-(5-chloroquinolin-8-yloxy)-acetic acid-(1-ethylpentyl) ester,
2-(5-chloroquinolin-8-yloxy)-acetic acid-(1-propylbutyl) ester,
2-(5-chloroquinolin-8-yloxy)-acetic acid-(1-pentylallyl) ester,
2-(5-chloroquinolin-8-yloxy)-acetic acid-(1-methylpentyl) ester,
2-(5-chloroquinolin-8-yloxy)-acetic acid-(1-methylisohexyl) ester,
2-(5-chloroquinolin-8-yloxy)-acetic acid-(1-phenylisobutyl) ester,
2-(5-chloroquinolin-8-yloxy)-acetic acid-(1-phenylethyl) ester,
2-(5-chloroquinolin-8-yloxy)-acetic acid-[1-methyl-2-(4-ethylphenoxy)-ethyl] ester,
2-(5-chloroquinolin-8-yloxy)-acetic acid-(1-methyl-2-phenylethyl) ester,
2-(5-chloroquinolin-8-yloxy)-acetic acid-(1-phenylpropyl) ester,
2-(5-chloroquinolin-8-yloxy)-acetic acid-(1-methyl-2-phenoxyethyl) ester,
2-(5-chloroquinolin-8-yloxy)-acetic acid-(1-methyl-3-phenylpropyl) ester, and
2-(5-chloroquinolin-8-yloxy)-acetic acid-[1-methyl-2-(4-methylphenoxy)-ethyl] ester.

The following compounds have proved particularly effective for this purpose:
2-(5-chloroquinolin-8-yloxy)-acetic acid methallyl ester,
2-(5-chloroquinolin-8-yloxy)-acetic acid-(2-phenoxyethyl) ester,
2-(5-chloroquinolin-8-yloxy)-acetic acid-(1-methylisopentyl) ester, and
2-(5-chloroquinolin-8-yloxy)-acetic acid-(1-methylhexyl) ester.

The following hitherto undisclosed individual active substances of the formula I have been synthesised specially for use as antidote to counteract the phytotoxic action of 2-[4-(5-chloro-3-fluoropyridin-2-yloxy)-phenoxy]-propionic acid derivatives. These active substances of the formula I form further subject matter of the present invention:
2-(5-chloroquinolin-8-yloxy)-acetic acid-(1-methylbutyl) ester,
2-(5-chloroquinolin-8-yloxy)-acetic acid-(1-ethylbutyl) ester,
2-(5-chloroquinolin-8-yloxy)-acetic acid-(1-methylisopentyl) ester,
2-(5-chloroquinolin-8-yloxy)-acetic acid-(1-methylhexyl) ester,
2-(5-chloroquinolin-8-yloxy)-acetic acid-(1-ethylpentyl) ester,
2-(5-chloroquinolin-8-yloxy)-acetic acid-(1-propylbutyl) ester,
2-(5-chloroquinolin-8-yloxy)-acetic acid-(1-pentylallyl) ester,
2-(5-chloroquinolin-8-yloxy)-acetic acid-(1-methylpentyl) ester,
2-(5-chloroquinolin-8-yloxy)-acetic acid-(R-1-methylisopentyl) ester,
2-(5-chloroquinolin-8-yloxy)-acetic acid-(S-1-methylisopentyl) ester,
2-(5-chloroquinolin-8-yloxy)-acetic acid-(R-1-methylhexyl) ester,
2-(5-chloroquinolin-8-yloxy)-acetic acid-(S-1-methylhexyl) ester,
2-(5-chloroquinolin-8-yloxy)-acetic acid-(1-methylisohexyl) ester,
2-(5-chloroquinolin-8-yloxy)-acetic acid-(1-phenylisobutyl) ester,
2-(5-chloroquinolin-8-yloxy)-acetic acid-(1-phenylethyl) ester,
2-(5-chloroquinolin-8-yloxy)-acetic acid-[1-methyl-2-(4-ethylphenoxy)-ethyl] ester,
2-(5-chloroquinolin-8-yloxy)-acetic acid-(1-methyl-2-phenylethyl) ester,
2-(5-chloroquinolin-8-yloxy)-acetic acid-(1-phenylpropyl) ester,
2-(5-chloroquinolin-8-yloxy)-acetic acid-(1-methyl-2-phenoxyethyl) ester,
2-(5-chloroquinolin-8-yloxy)-acetic acid-(1-methyl-3-phenylpropyl) ester, and
2-(5-chloroquinolin-8-yloxy)-acetic acid-[1-methyl-2-(4-methylphenoxy)-ethyl] ester.

These novel compounds are produced, in a manner known per se, from a 2-(5-chloroquinolin-8-yloxy)-acetic acid derivative and a suitable alcohol by esterification; or from 5-chloro-8-hydroxyquinoline and a suitable α-haloacetic acid ester in the presence of a base. Further suitable production processed are described in the published European Patent Application No. EP-A-94 349.

Optically active isomers of the compounds of the formula I can be obtained from the isomeric mixtures by customary isomer separation processes. The pure isomers are however advantageously produced by a specific synthesis from already optically active intermediates. For example, a suitable 2-(5-chloroquinolin-8-yloxy)-acetic acid derivative can be esterified with an optically active alcohol, or the coupling of 5-chloro-8-hydroxy-quinoline with an optically active α-haloacetic acid ester is performed.

Examples of compounds to be used according to the present invention, which compounds have a protective action against herbicidally active 2-[4-(5-chloro-3-fluoro-pyridin-2-yloxy)-phenoxy]-propionic acid derivatives, are contained in the following Table 1.

TABLE 1

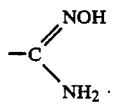

| No. | R¹ | R² | R³ | R⁴ | R⁵ | R⁶ | A | Z | Physical constants [m.p. °C.] |
|---|---|---|---|---|---|---|---|---|---|
| 1.1 | H | H | H | H | H | H | $-CH_2-$ | $-CN$ | 118–119° C. |
| 1.2 | H | H | H | H | H | H | $-CH_2-$ | $-C(=NOH)NH_2$ | 201–204° C. (decomp.) |
| 1.3 | H | H | H | H | H | CH₃ | $-CH_2-$ | $-CN$ | 114–116° C. |
| 1.4 | H | H | H | H | H | CH₃ | $-CH_2-$ | $-C(=NOH)NH_2$ | 209–210° C. (decomp.) |
| 1.5 | H | H | Cl | H | H | H | $-CH_2-$ | $-C(=NOH)NH_2$ | 203–205° C. (decomp.) |
| 1.6 | H | H | H | H | H | H | $-CH_2-$ | $-C(NH_2)=N-O-C(=O)-NH-C_3H_7\text{-}i$ | 136–138° C. |
| 1.7 | H | H | Cl | H | H | H | $-CH_2-$ | $-CN$ | 159–160° C. |
| 1.8 | H | H | H | H | H | H | $-CH_2-$ | $-C(NH_2)=N-O-C(=O)-CH_2Cl$ | 129–130° C. |
| 1.9 | Br | H | Cl | H | H | H | $-CH_2-$ | $-C(=NOH)NH_2$ | 197–198° C. (decomp.) |
| 1.10 | Br | H | Cl | H | H | H | $-CH_2-$ | $-CN$ | 150–151° C. |
| 1.11 | H | H | H | H | H | H | $-CH_2-$ | $-C(NH_2)=N-O-C(=O)-OCH_3$ | 143–145° C. |
| 1.12 | J | H | Cl | H | H | H | $-CH_2-$ | $-C(=NOH)NH_2$ | 195–196° C. (decomp.) |
| 1.13 | J | H | Cl | H | H | H | $-CH_2-$ | $-CN$ | 150.5–152° C. |
| 1.14 | Br | H | Cl | H | H | H | $-CH_2-$ | $-C(NH_2)=N-O-C(=O)-NH-C_3H_7\text{-}i$ | 162–165° C. |

TABLE 1-continued

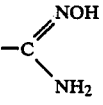

| No. | R¹ | R² | R³ | R⁴ | R⁵ | R⁶ | A | Z | Physical constants [m.p. °C.] |
|---|---|---|---|---|---|---|---|---|---|
| 1.15 | Cl | H | Cl | H | H | CH₃ | —CH₂— | -C(=NOH)NH₂ | 205-207° C. (decomp.) |
| 1.16 | Cl | H | Cl | H | H | H | —CH₂— | —CN | 150-152° C. |
| 1.17 | J | H | Cl | H | H | H | —CH₂— | -C(NH₂)=N-O-C(=O)-NH-C₃H₇-i | 163-167° C. |
| 1.18 | Cl | H | Cl | H | H | CH₃ | —CH₂— | —CN | 157-158° C. |
| 1.19 | Cl | H | Cl | H | H | CH₃ | —CH₂— | -C(NH₂)=N-O-C(=O)-NH-C₃H₇-i | 149-152° C. |
| 1.20 | H | H | H | H | H | H | —CH₂CH₂— | —CN | 108-112° C. |
| 1.21 | H | H | H | H | H | H | —CH(CH₃)— | —CN | 121-124° C. |
| 1.22 | H | H | H | H | H | H | —CH₂CH₂— | -C(=NOH)NH₂ | 186-189° C. |
| 1.23 | H | H | Cl | H | H | H | —CH(CH₃)— | —CN | 143-145° C. |
| 1.24 | H | H | H | H | H | H | —CH(CH₃)— | -C(=NOH)NH₂ | 191-194° C. (decomp.) |
| 1.25 | H | H | Cl | H | H | H | —CH(CH₃)— | -C(=NOH)NH₂ | 186-189° C. (decomp.) |
| 1.26 | H | H | NO₂ | H | H | H | —CH(CH₃)— | —CN | 154-156° C. |
| 1.27 | Cl | H | NO₂ | H | H | H | —CH₂— | -C(=NOH)NH₂ | 214-216° C. (decomp.) |
| 1.28 | Cl | H | NO₂ | H | H | H | —CH₂— | —CN | 166-169° C. |

TABLE 1-continued

Structure:

```
      R3   R4
   R2 \   / R5
      [ring]
   R1 /   \ R6
      |    N
      O-A-Z
```

| No. | R¹ | R² | R³ | R⁴ | R⁵ | R⁶ | A | Z | Physical constants [m.p. °C.] |
|---|---|---|---|---|---|---|---|---|---|
| 1.29 | H | H | H | H | H | H | —CH₂— | —C(NH₂)=N—O—C(=O)—C₃H₅—cycl. | 165–166° C. |
| 1.30 | H | H | H | H | H | H | —CH₂— | —C(NH₂)=N—O—C(=O)—C₆H₄—Cl (p) | 139–141° C. |
| 1.31 | H | H | Cl | H | H | H | —CH₂— | —C(NH₂)=N—O—C(=O)—CH₃ | 141–143° C. |
| 1.32 | H | H | NO₂ | H | H | H | —CH₂— | —CN | 162–164° C. |
| 1.33 | H | H | NO₂ | H | H | H | —CH₂— | —C(NH₂)=N—OH | 212–215° C. (decomp.) |
| 1.34 | H | H | Cl | H | H | H | —CH₂— | —C(NH₂)=N—O—C(=O)—OCH₃ | 148–149° C. |
| 1.35 | H | H | Cl | H | H | H | —CH₂— | —C(NH₂)=N—O—C(=O)—O—C₂H₅ | 139–140° C. |
| 1.36 | H | H | H | H | H | H | —CH₂— | —C(NH₂)=N—O—C(=O)—S—C₅H₁₁-n | 111–114° C. |
| 1.37 | H | H | H | H | H | H | —CH₂— | —C(NH₂)=N—O—C(=O)—CH=CH—CH₃ | 158–162° C. |

TABLE 1-continued
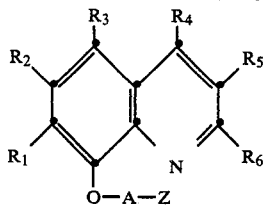
| No. | R¹ | R² | R³ | R⁴ | R⁵ | R⁶ | A | Z | Physical constants [m.p. °C.] |
|---|---|---|---|---|---|---|---|---|---|
| 1.38 | H | H | H | H | H | H | —CH₂— | —C(NH₂)=N—O—C(=O)—NH—C₂H₅ | 123–125° C. |
| 1.39 | H | H | H | H | H | H | —CH₂— | —C(NH₂)=N—O—C(=O)—N(CH₃)(OCH₃) | 138–139° C. |
| 1.40 | H | H | H | H | H | H | —CH₂— | —C(NH₂)=N—O—C(=O)—C₄H₉—n | 120–122° C. |
| 1.41 | H | H | Cl | H | H | H | —CH₂— | —C(NH₂)=N—O—C(=O)—C₂H₅ | 157–158° C. (decomp.) |
| 1.42 | H | H | H | H | H | H | —CH₂— | —C(NH₂)=N—O—C(=O)—CH₂CH₂CH₂Cl | 144–146° C. |
| 1.43 | H | H | H | H | H | H | —CH₂— | —C(NH₂)=N—O—C(=O)—CHCl—CH₂Cl | 112–114° C. |
| 1.44 | H | H | Cl | H | H | H | —CH₂— | —C(NH₂)=N—O—C(=O)—C₃H₇—i | 173–174° C. |
| 1.45 | H | H | H | H | H | H | —CH₂— | —C(NH₂)=N—O—C(=O)—O—C₆H₅ | 155–156° C. |

TABLE 1-continued
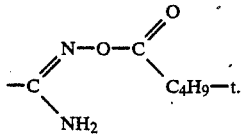
| No. | R¹ | R² | R³ | R⁴ | R⁵ | R⁶ | A | Z | Physical constants [m.p. °C.] |
|---|---|---|---|---|---|---|---|---|---|
| 1.46 | H | H | H | H | H | H | —CH₂— | 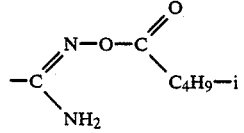 | 107–110.5° C. |
| 1.47 | H | H | H | H | H | H | —CH₂— | 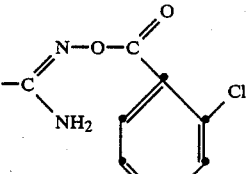 | 124–126° C. |
| 1.48 | H | H | H | H | H | H | —CH₂— | 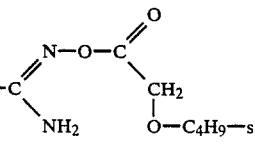 | 131–132° C. |
| 1.49 | H | H | H | H | H | H | —CH₂— | 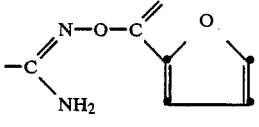 | 84–86° C. |
| 1.50 | H | H | H | H | H | H | —CH₂— | 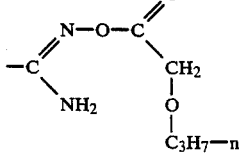 | 168–169° C. |
| 1.51 | H | H | H | H | H | H | —CH₂— | 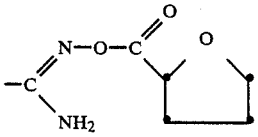 | 100–103° C. |
| 1.52 | H | H | Cl | H | H | H | —CH₂— | 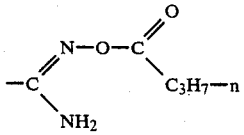 | 156–157° C. (decomp.) |
| 1.53 | H | H | H | H | H | H | —CH₂— |  | 82–85° C. |

TABLE 1-continued

Structure: benzene ring with substituents $R_1$, $R_2$, $R_3$ and $O-A-Z$ fused to a pyridine ring with $R_4$, $R_5$, $R_6$ substituents.

| No. | $R^1$ | $R^2$ | $R^3$ | $R^4$ | $R^5$ | $R^6$ | A | Z | Physical constants [m.p. °C] |
|---|---|---|---|---|---|---|---|---|---|
| 1.54 | H | H | H | H | H | H | —CH$_2$— | $-C(NH_2)=N-O-C(=O)-C_3H_7$-n | 144–147° C. |
| 1.55 | H | H | H | H | H | H | —CH$_2$— | $-C(NH_2)=N-O-C(=O)-C(CH_3)=CH_2$ | 128–130° C. |
| 1.56 | H | H | H | H | H | H | —CH$_2$— | $-C(NH_2)=N-O-C(=O)-NH-C_4H_9$-n | 104–107° C. |
| 1.57 | H | H | H | H | H | H | —CH$_2$— | $-C(NH_2)=N-O-C(=O)-CH_2Br$ | 132–134° C. |
| 1.58 | H | H | H | H | H | H | —CH$_2$— | $-C(NH_2)=N-O-C(=O)-CH=CH_2$ | 138–140° C. |
| 1.59 | H | H | H | H | H | H | —CH$_2$— | $-C(NH_2)=N-O-C(=O)-$(tetrahydrofuranyl) | 129–131° C. |
| 1.60 | H | H | H | H | H | H | —CH$_2$— | $-C(NH_2)=N-O-C(=O)-O-C_4H_9$-n | 121–123° C. |
| 1.61 | H | H | H | H | H | H | —CH$_2$— | $-C(NH_2)=N-O-C(=O)-O-CH_2-CH=CH_2$ | 123–125° C. |
| 1.62 | H | H | H | H | H | H | —CH$_2$— | $-C(NH_2)=N-O-C(=O)-O-CH_2-CH_2Br$ | 127–128° C. (decomp.) |

TABLE 1-continued
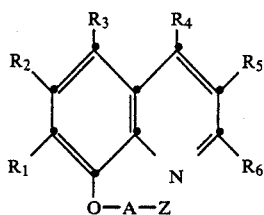
| No. | R¹ | R² | R³ | R⁴ | R⁵ | R⁶ | A | Z | Physical constants [m.p. °C.] |
|---|---|---|---|---|---|---|---|---|---|
| 1.63 | H | H | Cl | H | H | H | —CH₂— | (C=NH₂)—N=O—C(=O)—C₃H₅—cycl. | 173–175° C. |
| 1.64 | H | H | H | H | H | H | —CH₂— | (C=NH₂)—N=O—C(=O)—O—CH₂—C₆H₅ | 135–137° C. |
| 1.65 | H | H | Cl | H | H | H | —CH₂— | (C=NH₂)—N=O—C(=O)—furyl | 191–192 (decomp.) |
| 1.66 | H | H | H | H | H | H | —CH₂— | (C=NH₂)—N=O—C(=O)—S—C₂H₅ | 120–121° C. |
| 1.67 | H | H | H | H | H | H | —CH₂— | (C=NH₂)—N=O—C(=O)—CH₂—O—CH₃ | 118–120° C. |
| 1.68 | H | H | Cl | H | H | H | —CH₂— | (C=NH₂)—N=O—C(=O)—NH—C₆H₄—Cl | 191–192° C. (dceomp.) |

TABLE 1-continued

| No. | R¹ | R² | R³ | R⁴ | R⁵ | R⁶ | A | Z | Physical constants [m.p. °C] |
|---|---|---|---|---|---|---|---|---|---|
| 1.69 | H | H | H | H | H | H | —CH$_2$— | —C(NH$_2$)=N—O—C(=O)—phenyl | 158–159° C. |
| 1.70 | H | H | H | H | H | H | —CH$_2$— | —C(NH$_2$)=N—O—C(=O)—C$_3$H$_7$-i | 115–117.5° C. |
| 1.71 | H | H | H | H | H | H | —CH$_2$— | —C(NH$_2$)=N—O—C(=O)—CH$_2$—phenyl | 140–142° C. |
| 1.72 | H | H | H | H | H | H | —CH$_2$— | —C(NH$_2$)=N—O—C(=O)—(2-thienyl) | 164–165° C. |
| 1.73 | H | H | H | H | H | H | —CH$_2$— | —C(NH$_2$)=N—O—C(=O)—O—C$_2$H$_5$ | 129–132° C. |
| 1.74 | H | H | H | H | H | H | —CH$_2$— | —C(NH$_2$)=N—O—C(=O)—NH—phenyl | 155–157.5° C. |

TABLE 1-continued

Structure: benzene ring with substituents R1, R2, R3 and O—A—Z group, connected to a CH=C(R4)—C(R5)=N—C(R6) chain

| No. | R¹ | R² | R³ | R⁴ | R⁵ | R⁶ | A | Z | Physical constants [m.p. °C.] |
|---|---|---|---|---|---|---|---|---|---|
| 1.75 | H | H | H | H | H | H | —CH₂— | —C(NH₂)=N—O—C(=O)—NH—(3-CF₃-phenyl) | 158–160° C. |
| 1.76 | H | H | Cl | H | H | H | —CH₂— | —C(NH₂)=N—O—C(=O)—CH₂Cl | 155–158° C. (decomp.) |
| 1.77 | H | H | H | H | H | H | —CH₂— | —C(NH₂)=N—O—C(=O)—C₂H₅ | 144–146° C. |
| 1.78 | H | H | H | H | H | H | —CH₂— | —C(NH₂)=N—O—C(=O)—S—C₃H₇-i | 123–124° C. |
| 1.79 | H | H | H | H | H | H | —CH₂— | —C(NH₂)=N—O—C(=O)—(3,6-dichloropyrazin-2-yl) | 173–176° C. (decomp.) |
| 1.80 | H | H | H | H | H | H | —CH₂— | —C(NH₂)=N—O—C(=O)—CH₂—CH₂Cl | 134–136° C. (decomp.) |
| 1.81 | H | H | H | H | H | H | —CH₂— | —C(NH₂)=N—O—C(=O)—CH₃ | 100–102° C. |

TABLE 1-continued

[Structure: substituted biphenyl-like compound with R1-R6 substituents, O-A-Z group, and N in ring]

| No. | R¹ | R² | R³ | R⁴ | R⁵ | R⁶ | A | Z | Physical constants [m.p. °C.] |
|---|---|---|---|---|---|---|---|---|---|
| 1.82 | H | H | H | H | H | H | —CH₂— | [structure: -C(NH₂)=N-O-C(=O)-NH-(2,5-dichlorophenyl)] | 197–199° C. |
| 1.83 | H | H | H | H | H | H | —CH₂— | [structure: -C(NH₂)=N-O-C(=O)-(5-bromofuran-2-yl)] | 170–171° C. |
| 1.84 | Cl | H | Cl | H | H | H | —CH(CH₃)— | —COOCH₃ | 65–66° C. |
| 1.85 | H | H | H | H | H | H | —CH(CH₃)— | —COOCH₃ | 70–72° C. |
| 1.86 | H | H | H | H | H | H | —CH₂— | —COOH.H₂O | 184–185° C. |
| 1.87 | H | H | H | H | H | H | —CH₂— | —COOCH₂CH₂OCH₃ | 80–82° C. |
| 1.88 | H | H | H | H | H | H | —CH₂— | —COOCH₃ | 46.5–67.0° C. |
| 1.89 | H | H | H | H | H | H | —CH₂— | —COOC₂H₅.H₂O | 56–59° C. |
| 1.90 | H | H | H | H | H | H | —CH(CH₃)— | —CONH(CH₂)₃OC₂H₅ | 54–56° C. |
| 1.91 | H | H | H | H | H | H | —CH(CH₃)— | —CONHC₂H₅ | 86–88° C. |
| 1.92 | H | H | H | H | H | H | —CH₂— | —COOC₃H₇—n | 28–31° C. |
| 1.93 | H | H | H | H | H | H | —CH₂— | —COOC₃H₇—i | $n_D^{23} = 1.5696$ |
| 1.94 | H | H | H | H | H | H | —CH₂— | —CONHCH₃.H₂O | 74–81° C. |
| 1.95 | H | H | H | H | H | H | —CH₂— | —CON(CH₃)₂ | 142–145° C. |
| 1.96 | H | H | H | H | H | H | —CH₂— | —CONHC₂H₅ | $n_D^{22.5} = 1.6002$ |
| 1.97 | H | H | H | H | H | H | —CH(CH₃)— | —CONH(CH₂)₃OH | 120–122° C. |
| 1.98 | H | H | H | H | H | H | —CH₂— | —COOCH₂CH₂OC₂H₅ | $n_D^{24} = 1.5673$ |
| 1.99 | H | H | H | H | H | H | —CH(CH₃)— | —CONHCH₂—(phenyl) | 88–90° C. |
| 1.100 | H | H | H | H | H | H | —CH₂— | —CONH(CH₂)₃CH₃ | 66–68°0 C. |

TABLE 1-continued

[Structure: benzene ring with substituents R1, R2, R3 and O-A-Z group, attached via CH=C(R4) to C(R5)=N-R6, with O-A-Z substituent]

| No. | R¹ | R² | R³ | R⁴ | R⁵ | R⁶ | A | Z | Physical constants [m.p. °C.] |
|---|---|---|---|---|---|---|---|---|---|
| 1.101 | H | H | H | H | H | H | —CH(CH₃)— | —CON(CH₃)(CH₂CH₂OH) | $n_D^{22}$ = 1.6054 |
| 1.102 | H | H | H | H | H | H | —CH₂— | —CON(CH₃)(CH₂CH₂OH) | 146–149° C. |
| 1.103 | H | H | H | H | H | H | —CH₂— | —COOCH₂-(tetrahydrofuran) | viscous substance |
| 1.104 | H | H | H | H | H | H | —CH(CH₃)— | —CONH(CH₂)₃.H₂O | 73–76° C. |
| 1.105 | H | H | H | H | H | H | —CH(CH₃)— | —CO—N(morpholino) | 120–121° C. |
| 1.106 | H | H | H | H | H | H | —CH(CH₃)— | —CON(CH₃)₂ | 105–111° C. |
| 1.107 | H | H | Cl | H | H | H | —CH₂— | —COOH | 232–233° C. |
| 1.108 | H | H | Cl | H | H | H | —CH₂— | —COOCH₂CH₂OCH₃ | 97–98° C. |
| 1.109 | H | H | Cl | H | H | H | —CH₂— | —COOCH₃ | 104–105.5° C. |
| 1.110 | H | H | Cl | H | H | H | —CH₂— | —COOC₂H₅ | 116–117° C. |
| 1.111 | H | H | Cl | H | H | H | —CH₂— | —COOC₃H₇—n | 108–109° C. |
| 1.112 | H | H | Cl | H | H | H | —CH₂— | —CON(CH₃)₂ | 135–136° C. |
| 1.113 | H | H | H | H | H | CH₃ | —CH₂— | —COOCH₃ | 58–66° C. |
| 1.114 | H | H | H | H | H | CH₃ | —CH₂— | —COOC₂H₅ | $n_D^{22.5}$ = 1.5762 |
| 1.115 | H | H | Cl | H | H | H | —CH₂— | —COOC₄H₉—t | 63–69° C. |
| 1.116 | H | H | H | H | H | H | —CH₂— | —COOC₄H₉—t | 69–70° C. |
| 1.117 | H | H | Cl | H | H | H | —CH₂— | —COOCH₂—C≡CH | 115–116° C. |
| 1.118 | H | H | Cl | H | H | H | —CH₂— | —COOC₃H₇—i | 147–148° C. |
| 1.119 | H | H | Cl | H | H | H | —CH₂— | —COOCH₂CH₂OC₂H₅ | 102–104° C. |
| 1.120 | H | H | Cl | H | H | H | —CH₂— | —COOCH₂—(phenyl) | 110–112° C. |
| 1.121 | H | H | Cl | H | H | H | —CH₂— | —COOCH₂—CH=CH₂ | 98–99° C. |
| 1.122 | H | H | Cl | H | H | H | —CH₂— | —COO(CH₂)₁₁CH₃ | 76–77° C. |
| 1.123 | H | H | Cl | H | H | H | —CH₂— | —COOC₄H₉—s | 110–111° C. |
| 1.124 | H | H | H | H | H | H | —CH₂— | —COO(CH₂)₇CH₃ | $n_D^{24}$ = 1.5419 |
| 1.125 | H | H | Cl | H | H | H | —CH₂— | —COOC₄H₉n | 90.5–92° C. |
| 1.126 | H | H | H | H | H | H | —CH₂— | —COO(CH₂)₁₁CH₃ | $n_D^{23}$ = 1.5232 |
| 1.127 | H | H | H | H | H | H | —CH₂— | —COOCH₂—CH=CH₂ | $n_D^{23}$ = 1.5885 |
| 1.128 | H | H | Cl | H | H | H | —CH₂— | —COO(CH₂)₇CH₃ | 87–88° C. |
| 1.129 | H | H | H | H | H | H | —CH₂— | —COOC₄H—n | $n_D^{22}$ = 1.5642 |

TABLE 1-continued

Structure: benzene ring with substituents $R_1$, $R_2$, $R_3$ and O—A—Z; attached to =C($R_4$)—C($R_5$)=N—$R_6$ side chain.

| No. | $R^1$ | $R^2$ | $R^3$ | $R^4$ | $R^5$ | $R^6$ | A | Z | Physical constants [m.p. °C.] |
|---|---|---|---|---|---|---|---|---|---|
| 1.130H | H | H | H | H | H | H | —CH$_2$— | —COOC$_4$H$_9$—s | red oil |
| 1.131H | H | H | Cl | H | H | H | —CH$_2$— | —COOCH$_2$CH$_2$Cl | 125–126° C. |
| 1.132H | H | H | H | H | H | H | —CH$_2$— | —COOCH$_2$—(phenyl) | $n_D^{23.5}$ = 1.6099 |
| 1.133H | H | H | Cl | H | H | H | —CH$_2$— | —COOCH$_2$—(tetrahydrofuran-2-yl, O in ring) | 101–103° C. |
| 1.134H | H | H | Cl | H | H | H | —CH$_2$— | —COS(CH$_2$)$_7$CH$_3$ | 53–54° C. |
| 1.135H | H | H | H | H | H | H | —CH$_2$— | —COOCH$_2$CH$_2$Cl | 109–110° C. |
| 1.136J | H | H | Cl | H | H | H | —CH$_2$— | —COOC$_4$H$_9$—t | 81–97° C. |
| 1.137J | H | H | Cl | H | H | H | —CH$_2$— | —COOC$_2$H$_5$ | 92–94° C. |
| 1.138J | H | H | Cl | H | H | H | —CH$_2$— | —COO(CH$_2$)$_{11}$CH$_3$ | 51–53° C. |
| 1.139J | H | H | Cl | H | H | H | —CH$_2$— | —COOCH$_3$ | 121–126° C. |
| 1.140J | H | H | Cl | H | H | H | —CH$_2$— | —COOCH$_2$CH$_2$Cl | 44–45° C. |
| 1.141J | H | H | Cl | H | H | H | —CH$_2$— | —COOCH$_2$—(phenyl) | 112–113° C. |
| 1.142J | H | H | Cl | H | H | H | —CH$_2$— | —COOC$_3$H$_7$—n | 71–73° C. |
| 1.143H | H | H | H | H | H | H | —CH$_2$— | —COOC$_4$H$_9$—i | $n_D^{22}$ = 1.5632 |
| 1.144H | H | H | H | H | H | H | —CH$_2$— | —COOCH(CH$_3$)CH$_2$CH$_2$CH$_3$ | $n_D^{22}$ = 1.5391 |
| 1.145H | H | H | H | H | H | H | —CH$_2$— | —COOCH(CH$_3$)(CH$_2$)$_5$CH$_3$ | $n_D^{22}$ = 1.5342 |
| 1.146H | H | H | H | H | H | H | —CH$_2$— | —CONH(CH$_2$)$_{11}$CH$_3$ | 56–61° C. |
| 1.147H | H | H | H | H | H | H | —CH$_2$— | —CONHCH$_2$CH$_2$—N(morpholino, O) | 94–99° C. |
| 1.148H | H | H | H | H | H | H | —CH$_2$— | —CONHCH$_2$CH$_2$CH$_2$OH | 138–139° C. |
| 1.149H | H | H | H | H | H | H | —CH$_2$— | —CONH—(phenyl)H | 104–106° C. |
| 1.150H | H | H | H | H | H | H | —CH$_2$— | —CON(morpholino, O) | 99–103° C. |
| 1.151H | H | H | H | H | H | H | —CH$_2$— | —CONHCH$_2$CH$_2$N(C$_2$H$_5$)$_2$ | $n_D^{23}$ = 1.5686 |

TABLE 1-continued

Structure:

R3, R4 on pyridine-fused system; R2, R5; R1, R6; O—A—Z substituent.

| No. | R¹ | R² | R³ | R⁴ | R⁵ | R⁶ | A | Z | Physical constants [m.p. °C.] |
|---|---|---|---|---|---|---|---|---|---|
| 1.152 | H | H | H | H | H | H | —CH₂— | —CON(CH₂CH₂OH)₂ | 144–146° C. |
| 1.153 | H | H | H | H | H | H | —CH₂— | —CONH(CH₂)₃N(CH₃)₂ | $n_D^{23}$ = 1.5766 |
| 1.154 | H | H | H | H | H | H | —CH₂— | —CON(CH₃)(C₄H₉—n) | $n_D^{22}$ = 1.5840 |
| 1.155 | H | H | H | H | H | H | —CH₂— | —CONHCH₂—C₆H₅ · H₂O | 70.5–73.5° C. |
| 1.156 | H | H | H | H | H | H | —CH₂— | —CONHCH(CH₂CH₃)(CH₂OH) | 150–151° C. |
| 1.157 | H | H | H | H | H | H | —CH₂— | —CON(C₄H₉—n)₂ · 2H₂O | 105–106° C. |
| 1.158 | H | H | H | H | H | H | —CH₂— | —CONHCH₂CH₂—N(piperidine) | $n_D^{26}$ = 1.5821 |
| 1.159 | H | H | H | H | H | H | —CH₂— | —CONH(CH₂)₃N(CH₂CH₂OH)₂ | 109–110° C. |
| 1.160 | H | H | H | H | H | H | —CH₂— | —CONHCH₂—CH=CH₂ · H₂O | 71–75° C. |
| 1.161 | H | H | H | H | H | H | —CH₂— | —CONHCH₂—(oxetane) · H₂O | 57–58° C. |
| 1.162 | H | H | H | H | H | H | —CH₂— | —CONH(CH₂)₃OC₂H₅ | 51–61° C. |
| 1.163 | H | H | H | H | H | H | —CH₂— | —CONHCH₂CH₂NHCH₂CH₂OH | 70–91° C. |
| 1.164 | H | Cl | H | H | H | H | —CH₂— | CONH(CH₂)₃OC₂H₅ | 85–88° C. |
| 1.165 | H | Cl | H | H | H | H | —CH₂— | —CON(CH₃)(CH₂CH₂OH) | 187–189° C. |
| 1.166 | H | Cl | H | H | H | H | —CH₂— | —CON(CH₂CH₂OH)₂ | 177–179° C. |

TABLE 1-continued

[Structure with R1, R2, R3 on benzene ring, R4, R5, R6 on the =N-containing group, O-A-Z substituent]

| No. | R¹ | R² | R³ | R⁴ | R⁵ | R⁶ | A | Z | Physical constants [m.p. °C.] |
|---|---|---|---|---|---|---|---|---|---|
| 1.167 | H | H | Cl | H | H | H | —CH₂— | —CON(morpholino) | 148–150° C. |
| 1.168 | H | H | Cl | H | H | H | —CH₂— | —CONHCH₂CH₂CH₂OH | 157–160° C. |
| 1.169 | H | H | Cl | H | H | H | —CH₂— | —CONHC₄H₉—n.H₂O | 87–90° C. |
| 1.170 | H | H | Cl | H | H | H | —CH₂— | —CONHC₂H₅ | 94–98° C. |
| 1.171 | H | H | Cl | H | H | H | —CH₂— | —CONHCH₂—(phenyl).½H₂O | 146–149° C. |
| 1.172 | H | H | H | H | H | CH₃ | —CH₂— | —CONH₂ | 193–196° C. |
| 1.173 | H | H | H | H | H | H | —CH₂— | —CONHNH₂.H₂O | 121–124° C. |
| 1.174 | H | H | H | H | H | H | —CH₂— | —COONa.H₂O | 140–142° C. |
| 1.175 | H | H | H | H | H | H | —CH₂— | —COOK.H₂O | >200° C. |
| 1.176 | H | H | H | H | H | H | —CH₂— | —COO⊖ ⊕HN(CH₃)₃ | 176–178° C. |
| 1.177 | H | H | H | H | H | H | —CH₂— | —COO⊖ ⊕HN(CH₂CH₂OH)₃ | 97–98° C. |
| 1.178 | H | H | Cl | H | H | H | —CH₂— | —COOK.H₂O | >260° C. |
| 1.179 | H | H | Cl | H | H | H | —CH₂— | —COONa.H₂O | >260° C. |
| 1.180 | H | H | H | H | H | H | —CH₂— | —COO⊖ ⊕HN(C₂H₅)₃ | 255–257° C. (decomp.) |
| 1.181 | H | H | Cl | H | H | H | —CH₂— | —COO⊖ ⊕NH₄ | 227–228° C. (decomp.) |
| 1.182 | H | H | Cl | H | H | H | —CH₂— | —COO⊖ ⊕HN(CH₂CH₂OH)₃ | 132–156° C. |
| 1.183 | H | H | Cl | H | H | H | —CH(CH₃)— | —COO—(2,4-dimethylphenyl) | 120–122° C. |
| 1.184 | H | H | Cl | H | H | H | —CH₂— | —COOCH(CH₃)(CH₂)₅CH₃ | 65–67° C. |
| 1.185 | H | H | Cl | H | H | H | —CH₂— | —COOCH₂CH=CH—CH₃ | 100–102° C. |
| 1.186 | H | H | Cl | H | H | H | —CH₂— | —COOCH₂—C(CH₃)=CH₂ | 94–95° C. |
| 1.187 | H | H | Cl | H | H | H | —CH₂— | —COOCH₂CH₂OC₃H₇—i | 70–72° C. |
| 1.188 | H | H | Cl | H | H | H | —CH₂— | —COOCH₂CH₂—O—(phenyl) | 79–80.5° C. |
| 1.189 | Br | H | Br | H | H | H | —CH₂— | —COOCH₃ | 143–145° C. |
| 1.190 | Br | H | Cl | H | H | H | —CH₂— | —COOC₃H₇—i | 71–73° C. |

TABLE 1-continued

[Structure: benzene ring with substituents R1, R2, R3 and O-A-Z group, connected to C=N with R4, R5, R6]

| No. | R¹ | R² | R³ | R⁴ | R⁵ | R⁶ | A | Z | Physical constants [m.p. °C.] |
|---|---|---|---|---|---|---|---|---|---|
| 1.191Br | H | Br | H | H | H | | —CH$_2$— | —COOC$_3$H$_7$—i | 47-51° C. |
| 1.192Cl | H | Cl | H | H | H | | —CH$_2$— | —COOC$_4$H$_9$—n | 42-43.5° C. |
| 1.193Br | H | Cl | H | H | H | | —CH$_2$— | —COOC$_4$H$_9$—n | ca. 28° C. |
| 1.194Cl | H | Cl | H | H | H | | —CH$_2$— | —COO(CH$_2$)$_7$CH$_3$ | ca. 30° C. |
| 1.195Br | H | Cl | H | H | H | | —CH$_2$— | —COO(CH$_2$)$_7$CH$_3$ | 41-42° C. |
| 1.196Br | H | Cl | H | H | H | | —CH$_2$— | —COOCH(CH$_3$)(CH$_2$)$_5$CH$_3$ | 46-48° C. |
| 1.197Cl | H | Cl | H | H | H | | —CH$_2$— | —COO(CH$_2$)$_{11}$CH$_3$ | 49-50° C. |
| 1.198Br | H | Cl | H | H | H | | —CH$_2$— | —COO(CH$_2$)$_{11}$CH$_3$ | 50-52° C. |
| 1.199Cl | H | Cl | H | H | H | | —CH$_2$— | —COOCH$_2$-C$_6$H$_5$ | 79-80° C. |
| 1.200Br | H | Cl | H | H | H | | —CH$_2$— | —COOCH$_2$-C$_6$H$_5$ | 100-102° C. |
| 1.201Br | H | Br | H | H | H | | —CH$_2$— | —COOCH$_2$-C$_6$H$_5$ | 101-104° C. |
| 1.202Br | H | Cl | H | H | H | | —CH$_2$— | —COOCH$_2$CH$_2$OCH$_3$ | 68-70° C. |
| 1.203Cl | H | Cl | H | H | H | | —CH$_2$— | —COOCH$_2$CH$_2$OC$_2$H$_5$ | 81-82° C. |
| 1.204Br | H | Cl | H | H | H | | —CH$_2$— | —COOCH$_2$CH$_2$OC$_2$H$_5$ | 71-72° C. |
| 1.205Br | H | Cl | H | H | H | | —CH$_2$— | —COOCH$_2$CH$_2$OC$_3$H$_7$—i | $n_D^{25}$ = 1.5763 |
| 1.206Br | H | Cl | H | H | H | | —CH$_2$— | —COOCH$_2$CH$_2$O-C$_6$H$_5$ | 80-82° C. |
| 1.207Cl | H | Cl | H | H | H | | —CH$_2$— | —COOCH$_2$-(furan) | 77-78° C. |
| 1.208Br | H | Cl | H | H | H | | —CH$_2$— | —COOCH$_2$-(furan) | 79-80° C. |
| 1.209Cl | H | Cl | H | H | H | | —CH$_2$— | —COOCH$_2$CH=CH$_2$ | 72-73° C. |
| 1.210Br | H | Cl | H | H | H | | —CH$_2$— | —COOCH$_2$CH=CH$_2$ | 66-68.5° C. |
| 1.211Br | H | Br | H | H | H | | —CH$_2$— | —COOCH$_2$CH=CH$_2$ | 78-79° C. |
| 1.212Br | H | Cl | H | H | H | | —CH$_2$— | —COOCH$_2$CH=CH—CH$_3$ | 60-64° C. |
| 1.213Cl | H | Cl | H | H | H | | —CH$_2$— | —COOCH$_2$—C(CH$_3$)=CH$_2$ | 62-65° C. |
| 1.214Br | H | Cl | H | H | H | | —CH$_2$— | —COOCH$_2$—C(CH$_3$)=CH$_2$ | 62-64° C. |

TABLE 1-continued

[Structure: benzene ring with substituents R1 (at position bearing O-A-Z), R2, R3, R4, R5, R6, with an adjacent N-containing ring]

| No. | R¹ | R² | R³ | R⁴ | R⁵ | R⁶ | A | Z | Physical constants [m.p. °C.] |
|---|---|---|---|---|---|---|---|---|---|
| 1.215 | Br | H | Cl | H | H | H | —CH₂— | —COO—⟨C₆H₅⟩ | 52–54° C. |
| 1.216 | H | H | Cl | H | H | H | —CH(CH₃)— | —COOC₃H₇—i | $n_D^{24}$ = 1.5642 |
| 1.217 | H | H | Cl | H | H | H | —CH(CH₃)— | —COO(CH₂)₇CH₃ | $n_D^{23}$ = 1.5356 |
| 1.218 | H | H | Cl | H | H | H | —CH(CH₃)— | —COOCH(CH₃)(CH₂)₅CH₃ | $n_D^{25}$ = 1.5370 |
| 1.219 | H | H | Cl | H | H | H | —CH(CH₃)— | —COO(CH₂)₁₁CH₃ | 54–55° C. |
| 1.220 | H | H | Cl | H | H | H | —CH(CH₃)— | —COOCH₂—⟨C₆H₅⟩ | 57–59° C. |
| 1.221 | H | H | Cl | H | H | H | —CH(CH₃)— | —COOCH₂CH₂OC₃H₇—i | $n_D^{32}$ = 1.5403 |
| 1.222 | H | H | Cl | H | H | H | —CH(CH₃)— | —COOCH₂CH₂O—⟨C₆H₅⟩ | $n_D^{29}$ = 1.5962 |
| 1.223 | H | H | Cl | H | H | H | —CH(CH₃)— | —COOCH₂CH=CH₂ | 40–41° C. |
| 1.224 | H | H | Cl | H | H | H | —CH(CH₃)— | —COOCH₂CH=CH—CH₃ | 39–40° C. |
| 1.225 | H | H | Cl | H | H | H | —CH(CH₃)— | —COOCH₂—C(CH₃)=CH₂ | 62–63° C. |
| 1.226 | H | H | Cl | H | H | H | —CH(CH₃)— | —COO—⟨C₆H₅⟩ | $n_D^{30}$ = 1.5677 |
| 1.227 | Br | H | Cl | H | H | H | —CH(CH₃)— | —COO(CH₂)₇CH₃ | $n_D^{28}$ = 1.5439 |
| 1.228 | Cl | H | Cl | H | H | H | —CH(CH₃)— | —COOCH(CH₃)(CH₂)₅CH₃ | $n_D^{25}$ = 1.5408 |

TABLE 1-continued

Structure: benzene ring with substituents R1, R2, R3 and O—A—Z group, connected via CH=CR4 to C(R5)=N—R6

| No. | R¹ | R² | R³ | R⁴ | R⁵ | R⁶ | A | Z | Physical constants [m.p. °C.] |
|---|---|---|---|---|---|---|---|---|---|
| 1.229 | Br | H | Cl | H | H | H | —CH(CH₃)— | —C(CH₃)H—COOCH(CH₂)₅CH₃ | $n_D^{25} = 1.5527$ |
| 1.230 | Br | H | Cl | H | H | H | —CH(CH₃)— | —COO(CH₂)₁₁CH₃ | $n_D^{30} = 1.5347$ |
| 1.231 | Br | H | Cl | H | H | H | —CH(CH₃)— | —COOCH₂—C₆H₅ | 55–56° C. |
| 1.232 | Br | H | Cl | H | H | H | —CH(CH₃)— | —COOCH₂—(tetrahydrofuryl, O) | $n_D^{30} = 1.5886$ |
| 1.223 | Br | H | Cl | H | H | H | —CH(CH₃)— | —COOCH₂CH₂OC₃H₇—i | $n_D^{28} = 1.5642$ |
| 1.234 | Br | H | Cl | H | H | H | —CH(CH₃)— | —COOCH₂CH₂O—C₆H₅ | $n_D^{20} = 1.6031$ |
| 1.235 | Br | H | Cl | H | H | H | —CH(CH₃)— | —COOCH₂CH=CH₂ | 55–56° C. |
| 1.236 | Cl | H | Cl | H | H | H | —CH(CH₃)— | —COOCH₂CH=CH—CH₃ | 38–39° C. |
| 1.237 | Br | H | Cl | H | H | H | —CH(CH₃)— | —COOCH₂CH=CH—CH₃ | 38–40° C. |
| 1.238 | Br | H | Cl | H | H | H | —CH(CH₃)— | —COOCH₂C(CH₃)=CH₂ | $n_D^{28} = 1.5824$ |
| 1.239 | H | H | Cl | H | H | H | —CH₂— | —COO—C₆H₅ | 165–170° C. |
| 1.240 | H | H | Cl | H | H | H | —CH₂— | —COO—C₆H₄—CH₃ (p) | 143–145° C. |
| 1.241 | H | H | Cl | H | H | H | —CH₂— | —COO—C₆H₄—CH₃ (o) | 111–116° C. |

TABLE 1-continued

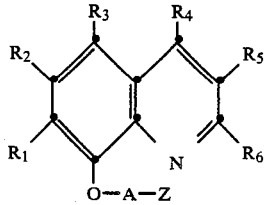

| No. | R¹ | R² | R³ | R⁴ | R⁵ | R⁶ | A | Z | Physical constants [m.p. °C.] |
|---|---|---|---|---|---|---|---|---|---|
| 1.242 | H | H | Cl | H | H | H | —CH₂— | 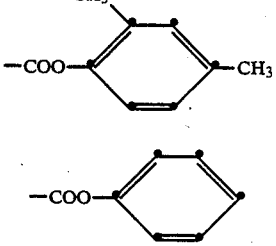 | 108–119° C. |
| 1.243 | H | H | Cl | H | H | H | —CH(CH₃)— | 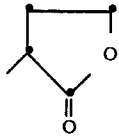 | 102–105° C. |
| 1.244 | H | H | Cl | H | H | H | | 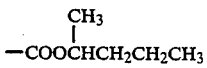 | 140–141.5° C. |
| 1.245 | H | H | Cl | H | H | H | —CH₂— | —COOCH(CH₃)CH₂CH₂CH₃ | 65–70° C. |
| 1.246 | H | H | H | H | H | H | —CH₂— | —COOCH₂—CH(CH₃)(CH₂)₂CH₃ | $n_D^{22} = 1.5525$ |
| 1.247 | H | H | Cl | H | H | H | —CH₂— | 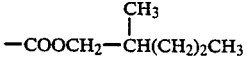 | 112–113° C. |
| 1.248 | H | H | Cl | H | H | H | —CH₂— | —COOCH₂CH(CH₃)—CH₃ | 113–114° C. |
| 1.249 | H | H | H | H | H | H | —CH₂— | —COO(CH₂)₂CH(OCH₃)CH₃ | $n_D^{22} = 1.5580$ |
| 1.250 | H | H | H | H | H | H | —CH₂— | —COOCH₂CH₂OCH₂CH₂O(CH₂)₃CH₃ | $n_D^{22} = 1.5389$ |
| 1.251 | H | H | H | H | H | H | —CH₂— | —COS(CH₂)₃CH₃ | $n_D^{23} = 1.6096$ |
| 1.252 | H | H | H | H | H | H | —CH₂— | 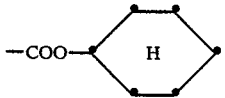 | $n_D^{23} = 1.5755$ |
| 1.253 | H | H | H | H | H | H | —CH₂— | —COO(CH₂)₄CH₃ | $n_D^{23} = 1.5591$ |
| 1.254 | H | H | H | H | H | H | —CH₂— | —COS(CH₂)₇CH₃ | $n_D^{22} = 1.5697$ |
| 1.255 | H | H | Cl | H | H | H | —CH₂— | —COOCH₂—CH(CH₃)(CH₂)₂CH₃ | 74–75° C. |
| 1.256 | H | H | Cl | H | H | H | —CH₂— | —COS(CH₂)₃CH₃ | $n_D^{22} = 1.6076$ |
| 1.257 | H | H | H | H | H | H | —CH₂— | —COOCH₂CH=CH—CH₃ | $n_D^{22} = 1.5833$ |
| 1.258 | H | H | H | H | H | H | —CH₂— | —COOCH₂—CH(C₂H₅)—C₂H₅ | $n_D^{23} = 1.5530$ |
| 1.259 | H | H | Cl | H | H | H | —CH₂— | —COOCH₂CH₂OCH₂CH₂O(CH₂)₃CH₃ | 39–41° C. |

TABLE 1-continued

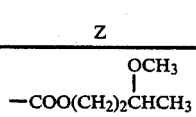

| No. | R¹ | R² | R³ | R⁴ | R⁵ | R⁶ | A | Z | Physical constants [m.p. °C.] |
|---|---|---|---|---|---|---|---|---|---|
| 1.260 | H | H | Cl | H | H | H | —CH₂— | —COO(CH₂)₂CHCH₃ with OCH₃ on CH | 72–73° C. |
| 1.261 | H | H | Cl | H | H | H | —CH₂— | —COO(CH₂)₄CH₃ | 78–79° C. |
| 1.262 | H | H | Cl | H | H | H | —CH₂— | —COOCH—(CH₂)₂CH₃ with C₂H₅ | 37–46° C. |
| 1.263 | H | H | H | H | H | H | —CH₂— | —COOCH₂CH₂OC₃H₇—i | $n_D^{22} = 1.5446$ |
| 1.264 | H | H | Cl | H | H | H | —CH₂— | —COO(CH₂)₁₃CH₃ | 75–76° C. |
| 1.265 | H | H | H | H | H | H | —CH₂— | —COOCH—C₂H₅ with C₂H₅ | 47–50° C. |
| 1.266 | H | H | H | H | H | H | —CH₂— | —COO-cyclohexyl (CH₃, H) | 29–31° C. |
| 1.267 | H | H | Cl | H | H | H | —CH₂— | —COOCH₂—CH—C₂H₅ with C₂H₅ | 58–63° C. |
| 1.268 | H | H | H | H | H | H | —CH₂— | —COOCH₂CH₂OCH₂CH₂OC₂H₅ | $n_D^{22} = 1.5489$ |
| 1.269 | H | H | H | H | H | H | —CH₂— | —COOCH₂CH₂O—phenyl | 80–81° C. |
| 1.270 | H | H | Cl | H | H | H | —CH₂— | —COOCH—C₂H₅ with C₂H₅ | 55–80° C. |
| 1.271 | H | H | H | H | H | H | —CH₂— | —COOCHCH₂CH—CH₃ with CH₃, CH₃ | $n_D^{22} = 1.5463$ |
| 1.272 | H | H | H | H | H | H | —CH₂— | —COO(CH₂)₁₃CH₃ | 35–36° C. |
| 1.273 | H | H | H | H | H | H | —CH₂— | —COOCH₂CH₂O(CH₂)₃CH₃ | $n_D^{22} = 1.5495$ |
| 1.274 | H | H | Cl | H | H | H | —CH₂— | —COOCH₂CH₂OCH₂CH₂OC₂H₅ | 42–43° C. |
| 1.275 | H | H | H | H | H | H | —CH₂— | —COOCH₂—CH—C₂H₅ with CH₃ | $n_D^{22} = 1.5566$ |
| 1.276 | H | H | Cl | H | H | H | —CH₂— | —COOCHCH₂CH—CH₃ with CH₃, CH₃ | 64–64° C. |
| 1.277 | H | H | H | H | H | H | —CH₂— | —COSCH—C₂H₅ with CH₃ | $n_D^{22} = 1.5973$ |
| 1.278 | H | H | Cl | H | H | H | —CH₂— | —COO-cyclohexyl (CH₃, H) | 98–101° C. |

TABLE 1-continued

Structure:
R1, R2, R3 on benzene ring; R4, R5, R6 on adjacent vinyl/pyridine ring; O—A—Z substituent

| No. | R¹ | R² | R³ | R⁴ | R⁵ | R⁶ | A | Z | Physical constants [m.p. °C.] |
|---|---|---|---|---|---|---|---|---|---|
| 1.279 | H | H | H | H | H | H | —CH$_2$— | —COOC(CH$_3$)(C$_2$H$_5$)C$_2$H$_5$ | $n_D^{22}$ = 1.5551 |
| 1.280 | H | H | H | H | H | H | —CH$_2$— | —COOCH$_2$—C(CH$_3$)=CH$_2$ | $n_D^{22}$ = 1.5805 |
| 1.281 | H | H | H | H | H | H | —CH$_2$— | —COOC(CH$_3$)(CH$_3$)—CH=CH$_2$ | $n_D^{22}$ = 1.5793 |
| 1.282 | H | H | H | H | H | H | —CH$_2$— | —COOCH$_2$CH$_2$OCH$_2$CH$_2$OCH$_3$ | $n_D^{23}$ = 1.5560 |
| 1.283 | H | H | Cl | H | H | H | —CH$_2$— | —COOC(CH$_3$)(C$_2$H$_5$)C$_2$H$_5$ | $n_D^{22}$ = 1.5632 |
| 1.284 | H | H | Cl | H | H | H | —CH$_2$— | —COO(CH$_2$)$_{10}$CH$_3$ | 70–71° C. |
| 1.285 | H | H | Cl | H | H | H | —CH$_2$— | —COOCH$_2$—CH(CH$_3$)—C$_2$H$_5$ | 78–79° C. |
| 1.286 | H | H | H | H | H | H | —CH$_2$— | —COO-cyclohexyl(CH$_3$) | 40–42° C. |
| 1.287 | H | H | H | H | H | H | —CH$_2$— | —COO(CH$_2$)$_6$CH$_3$ | $n_D^{23}$ = 1.5469 |
| 1.288 | H | H | H | H | H | H | —CH$_2$— | —COOC(CH$_3$)(CH$_3$)C$_2$H$_5$ | $n_D^{22}$ = 1.5881 |
| 1.289 | H | H | Cl | H | H | H | —CH$_2$— | —COOCH$_2$CH$_2$O(CH$_2$)$_3$CH$_3$ | 69–70° C. |
| 1.290 | H | H | Cl | H | H | H | —CH$_2$— | —COSCH(CH$_3$)—C$_2$H$_5$ | 55–56° C. |
| 1.291 | H | H | Cl | H | H | H | —CH$_2$— | —COOC(CH$_3$)(CH$_3$)—CH=CH$_2$ | 83–87° C. |
| 1.292 | H | H | H | H | H | H | —CH$_2$— | —COSCH$_3$ | 41–44° C. |
| 1.293 | H | H | Cl | H | H | H | —CH$_2$— | —COOCH$_2$CH$_2$OCH$_2$CH$_2$OCH$_3$ | $n_D^{22}$ = 1.5633 |
| 1.294 | H | H | Cl | H | H | H | —CH$_2$— | —COSCH$_3$ | 89–91° C. |
| 1.295 | H | H | Cl | H | H | H | —CH$_2$— | —COOC(CH$_3$)(C$_2$H$_5$)CH$_3$ | 53–54° C. |
| 1.296 | H | H | H | H | H | H | —CH$_2$— | —COO(CH$_2$)$_{10}$CH$_3$ | $n_D^{23}$ = 1.5310 |
| 1.297 | H | H | Cl | H | H | H | —CH$_2$— | —COO(CH$_2$)$_6$CH$_3$ | 74–76° C. |
| 1.298 | H | H | H | H | H | H | —CH$_2$— | —COOCH(CH$_3$)—CH(CH$_3$)—CH$_3$ | $n_D^{23}$ = 1.5554 |

TABLE 1-continued

[Structure: benzene ring with R1, R2, R3 substituents and O-A-Z, connected to C(R4)=C(R5)-N=... with R6]

| No. | R¹ | R² | R³ | R⁴ | R⁵ | R⁶ | A | Z | Physical constants [m.p. °C.] |
|---|---|---|---|---|---|---|---|---|---|
| 1.299 | H | H | Cl | H | H | H | —CH₂— | —COO—⟨cyclohexyl with H, CH₃⟩ | 103–105° C. |
| 1.300 | H | H | H | H | H | H | —CH₂— | —COSC(CH₃)₃ | $n_D^{23}$ = 1.5987 |
| 1.301 | H | H | Cl | H | H | H | —CH₂— | —COS(CH₂)₁₁CH₃ | 26–28° C. |
| 1.302 | H | H | Cl | H | H | H | —CH₂— | —COS(CH₂)₉CH₃ | 29–31°C. |
| 1.303 | H | H | Cl | H | H | H | —CH₂— | —COO(CH₂)₉CH₃ | 73–74° C. |
| 1.304 | H | H | H | H | H | H | —CH₂— | —COOCH(CH₃)(CH₂)₄CH₂ | $n_D^{23}$ = 1.5433 |
| 1.305 | H | H | Cl | H | H | H | —CH₂— | —COOCH(C₃H₇-n)—C≡CH | 81–82° C. |
| 1.306 | H | H | H | H | H | H | —CH₂— | —COOCH(C₅H₁₁-n)—CH=CH₂ | $n_D^{23}$ = 1.5472 |
| 1.307 | H | H | Cl | H | H | H | —CH₂— | —COOCH(CH₃)—CH(CH₃)—CH₃ | 70–74° C. |
| 1.308 | H | H | Cl | H | H | H | —CH₂— | —COSC(CH₃)₃ | $n_D^{22}$ = 1.5996 |
| 1.309 | H | H | H | H | H | H | —CH₂— | —COOCH(CH₃)—C≡CH | $n_D^{23}$ = 1.5837 |
| 1.310 | H | H | H | H | H | H | —CH₂— | —COS(CH₂)₁₁CH₃ | $n_D^{23}$ = 1.5523 |
| 1.311 | H | H | H | H | H | H | —CH₂— | —COOCH₂—C(CH₃)₃ | $n_D^{22}$ = 1.5524 |
| 1.312 | H | H | H | H | H | H | —CH₂— | —COSC₂H₅ | $n_D^{23}$ = 1.6310 |
| 1.313 | H | H | Cl | H | H | H | —CH₂— | —COOCH₂—C(CH₃)₃ | 76–81° C. |
| 1.314 | H | H | Cl | H | H | H | —CH₂— | —COSC₃H₇-n | $n_D^{22}$ = 1.6136 |
| 1.315 | H | H | H | H | H | H | —CH₂— | —COO(CH₂)₉CH₃ | $n_D^{22}$ = 1.5308 |
| 1.316 | H | H | Cl | H | H | H | —CH₂— | —COOCH(CH₃)(CH₂)₄CH₃ | 65–67° C. |
| 1.317 | H | H | H | H | H | H | —CH₂— | —COO(CH₂)₂CH(CH₃)—CH₃ | $n_D^{23}$ = 1.5568 |

TABLE 1-continued

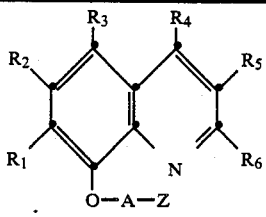

| No. | R¹ | R² | R³ | R⁴ | R⁵ | R⁶ | A | Z | Physical constants [m.p. °C.] |
|---|---|---|---|---|---|---|---|---|---|
| 1.318H | H | H | H | H | H | H | $-CH_2-$ | $-COOCH(CH_2)_3CH_3$ with $C_2H_5$ | $n_D^{22} = 1.5454$ |
| 1.319H | H | H | Cl | H | H | H | $-CH_2-$ | $-COO(CH_2)_8CH_3$ | 78–79° C. |
| 1.320H | H | H | H | H | H | H | $-CH_2-$ | $-COSCH_2CHCH_3$ with $CH_3$ | $n_D^{23} = 1.6049$ |
| 1.321H | H | H | Cl | H | H | H | $-CH_2-$ | $-COSC_2H_5$ | 55–57° C. |
| 1.322H | H | H | H | H | H | H | $-CH_2-$ | $-COO(CH_2)_8CH_3$ | $n_D^{24} = 1.5436$ |
| 1.323H | H | H | Cl | H | H | H | $-CH_2-$ | $-COOCH_2-CH(CH_2)_3CH_3$ with $C_2H_5$ | 45–47° C. |
| 1.324H | H | H | Cl | H | H | H | $-CH_2-$ | $-COSCH_2CH-CH_3$ with $CH_3$ | $n_D^{23} = 1.6045$ |
| 1.325H | H | H | H | H | H | H | $-CH_2-$ | $-COS(CH_2)_9CH_3$ | $n_D^{23} = 1.5630$ |
| 1.326H | H | H | Cl | H | H | H | $-CH_2-$ | $-COO(CH_2)_2CH-CH_3$ with $CH_3$ | 72–74° C. |
| 1.327H | H | H | Cl | H | H | H | $-CH_2-$ | $-COOCH(CH_2)_3CH_3$ with $C_2H_5$ | $n_D^{22} = 1.5542$ |
| 1.328H | H | H | H | H | H | H | $-CH_2-$ | $-COO(CH_2)_5CH_3$ | $n_D^{22} = 1.5512$ |
| 1.329H | H | H | H | H | H | H | $-CH_2-$ | $-COOCH(CH_2)_2CH_3$ with $C_3H_7-n$ | 48–50° C. |
| 1.330H | H | H | H | H | H | H | $-CH_2-$ | $-COS(CH_2)_4CH_3$ | $n_D^{22} = 1.5937$ |
| 1.331H | H | H | H | H | H | H | $-CH_2-$ | $-COSC_3H_7-iso$ | $n_D^{23} = 1.5821$ |
| 1.332H | H | H | H | H | H | H | $-CH_2-$ | $-COOCH_2CH-(CH_2)_3CH_3$ with $C_2H_5$ | $n_D^{22} = 1.5395$ |
| 1.333H | H | H | Cl | H | H | H | $-CH_2-$ | $-COOCH(CH_2)_2CH_3$ with $C_3H_7-n$ | 55–57° C. |
| 1.334H | H | H | Cl | H | H | H | $-CH_2-$ | $COS(CH_2)_5CH_3$ | $n_D^{22} = 1.5882$ |
| 1.335H | H | H | Cl | H | H | H | $-CH_2-$ | $-COS(CH_2)_4CH_3$ | $n_D^{23} = 1.5990$ |
| 1.336H | H | H | Cl | H | H | H | $-CH_2-$ | $-COO(CH_2)_5CH_3$ | 71–72° C. |
| 1.337H | H | H | Cl | H | H | H | $-CH_2-$ | $-COSC_3H_7-iso$ | 62–64° C. |
| 1.338H | H | H | Cl | H | H | H | $-CH_2-$ | $-COOCH-CH_2CHC_2H_5$ with $C_2H_5$, $CH_3$ | 25–29° C. |
| 1.339H | H | H | H | H | H | H | $-CH_2-$ | $-COOCH-C_3H_7-i$ with $C_3H_7-i$ | $n_D^{22} = 1.5468$ |
| 1.340H | H | H | H | H | H | H | $-CH_2-$ | $-COOCH-(CH_2)_3CH_3$ with $CH_3$ | $n_D^{23} = 1.5531$ |
| 1.341H | H | H | Cl | H | H | H | $-CH_2-$ | $-COOCH-CH=CH_2$ with $C_5H_{11}-n$ | $n_D^{23} = 1.5579$ |

TABLE 1-continued $$\begin{array}{c}\text{structure with } R_1, R_2, R_3 \text{ on benzene ring, } R_4, R_5, R_6 \text{ on pyridine ring, O-A-Z substituent}\end{array}$$

| No. | $R^1$ | $R^2$ | $R^3$ | $R^4$ | $R^5$ | $R^6$ | A | Z | Physical constants [m.p. °C.] |
|---|---|---|---|---|---|---|---|---|---|
| 1.342 | H | H | H | H | H | H | —CH$_2$— | —COOCH(C$_2$H$_5$)—(CH$_2$)$_2$CH$_3$ | 42–44° C. |
| 1.343 | H | H | H | H | H | H | —CH$_2$— | —COSC$_3$H$_7$—n | $n_D^{22}$ = 1.6108 |
| 1.344 | H | H | Cl | H | H | H | —CH$_2$— | —COOCH(CH$_3$)—(CH$_2$)$_3$CH$_3$ | 68–71° C. |
| 1.345 | H | H | H | H | H | H | —CH$_2$— | —COOCH(C$_2$H$_5$)CH$_2$CH(CH$_3$)C$_2$H$_5$ | $n_D^{23}$ = 1.5472 |
| 1.346 | H | H | Cl | H | H | H | —CH$_2$— | —COOCH(C$_3$H$_7$—i)—C$_3$H$_7$—i | 88–89° C. |
| 1.347 | H | H | H | H | H | H | —CH$_2$— | —COS(CH$_2$)$_5$CH$_3$ | $n_D^{22}$ = 1.5804 |
| 1.348 | H | H | H | H | H | H | —CH$_2$— | —COO(CH$_2$)$_9$—CH=CH$_2$ | $n_D^{22}$ = 1.5386 |
| 1.349 | H | H | H | H | H | H | —CH$_2$— | —COOCH(C$_3$H$_7$—n)—C≡CH | $n_D^{22}$ = 1.5659 |
| 1.350 | H | H | Cl | H | H | H | —CH$_2$— | —COOCH(CH$_3$)—C≡CH | 97–100° C. |
| 1.351 | H | H | H | H | H | H | —CH$_2$— | —COOC(CH$_3$)(C$_2$H$_5$)—C≡CH | $n_D^{22}$ = 1.5688 |
| 1.352 | H | H | Cl | H | H | H | —CH$_2$— | —COO(CH$_2$)$_9$—CH=CH$_2$ | 66–67° C. |
| 1.353 | H | H | Cl | H | H | H | —CH$_2$— | —COO—C(CH$_3$)(CH$_3$)—C≡CH | 76–81° C. |
| 1.354 | H | H | H | H | H | H | —CH$_2$— | —COO—C(CH$_3$)(CH$_3$)—C≡CH | $n_D^{23}$ = 1.5740 |
| 1.355 | H | H | Cl | H | H | H | —CH$_2$— | —COO—C(CH$_3$)(C$_2$H$_5$)—C≡CH | 78–79° C. |
| 1.356 | H | H | Cl | H | H | H | —CH$_2$— | —COO—CH(CH$_3$)—CH(CH$_3$)—C$_2$H$_5$ | 71–73° C. |
| 1.357 | Br | H | Cl | H | H | H | —CH$_2$— | —COOCH$_3$ | 126–128° C. |
| 1.358 | Br | H | Cl | H | H | H | —CH(CH$_3$)— | —COOC$_3$H$_7$—i | 66–68° C. |
| 1.359 | Cl | H | Cl | H | H | H | —CH$_2$— | —COOCH$_2$CH$_2$OCH$_3$ | 68–70° C. |
| 1.360 | Cl | H | Cl | H | H | H | —CH$_2$— | —COOC$_3$H$_7$—i | 60–63° C. |

TABLE 1-continued

Structure:
R1, R2, R3 on benzene ring; R4, R5, R6 on the =CH-C(R5)=N-C(R6) part; O-A-Z on the ring.

| No. | R¹ | R² | R³ | R⁴ | R⁵ | R⁶ | A | Z | Physical constants [m.p. °C.] |
|---|---|---|---|---|---|---|---|---|---|
| 1.361 | H | H | Cl | H | H | H | —CH(CH₃)— | —COOCH₂-(oxiranyl) | $n_D^{30}$ = 1.5734 |
| 1.362 | H | H | Cl | H | H | H | —CH₂— | —COOCH₂COOC₄H₉—n | 52–54° C. |
| 1.363 | H | H | Cl | H | H | H | —CH₂— | —COOCH(CH₃)—COOC₄H₉—n | $n_D^{22}$ = 1.5508 |
| 1.364 | H | H | Cl | H | H | H | —CH₂— | —COOCH(CH₃)CH₂CH₂CH(CH₃)—CH₃ | 55–59° C. |
| 1.365 | H | H | Cl | H | H | H | —CH₂— | —COOCH(C₃H₇—i)-phenyl | 43–47° C. |
| 1.366 | H | H | Cl | H | H | H | —CH₂— | —COOCH(CH₃)CH₂O-(2-CH₃-phenyl) | 75–78° C. |
| 1.367 | H | H | Cl | H | H | H | —CH₂— | —COOCH(CH₃)-phenyl | 117–122° C. |
| 1.368 | H | H | Cl | H | H | H | —CH₂— | —COOCH(CH₃)CH₂O-(4-C₂H₅-phenyl) | 63–68° C. |
| 1.369 | H | H | Cl | H | H | H | —CH₂— | —COOCH(CH₃)CH₂-phenyl | 116–118° C. |
| 1.370 | H | H | Cl | H | H | H | —CH₂— | —COOCH(CH₃)—CH₂O-(2-C₃H₇—i-phenyl) | 41–43° C. |
| 1.371 | H | H | Cl | H | H | H | —CH₂— | —COOCH(C₂H₅)-phenyl | 74–76° C. |
| 1.372 | H | H | Cl | H | H | H | —CH₂— | —COOCH(CH₃)CH₂O-(2-C₂H₅-phenyl) | 96–98° C. |

TABLE 1-continued

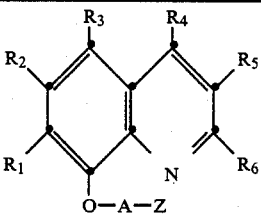

| No. | R¹ | R² | R³ | R⁴ | R⁵ | R⁶ | A | Z | Physical constants [m.p. °C.] |
|---|---|---|---|---|---|---|---|---|---|
| 1.373 | H | H | Cl | H | H | H | —CH₂— | —COOCHCH₂O—(C₆H₄)—C₂H₅ | 82–85° C. |
| 1.374 | H | H | Cl | H | H | H | —CH₂— | —COOCH(CH₃)CH₂O—(C₆H₅) | 42–44° C. |
| 1.375 | H | H | Cl | H | H | H | —CH₂— | —COOCH(CH₃)CH₂CH₂—(C₆H₅) | 78–79° C. |
| 1.376 | H | H | Cl | H | H | H | —CH₂— | —COOCH(CH₃)CH₂O—(C₆H₄)—CH₃ | 58–61° C. |
| 1.377 | H | H | Cl | H | H | H | —CH₂— | —COOCH(CH₃)CH₂O—(C₆H₄)—C₃H₇—i | 35–38° C. |
| 1.378 | H | H | Cl | H | H | H | —CH₂— | —COOCH(CH₃)CH₂O—(C₆H₄)—CH₃ | 82–84° C. |

The compounds of the formula I can be produced by known methods, such as are described for example in the European Patent Publication Nos. 86,750 and 94,349, or they can be obtained by methods analogous to known methods.

The quinoline derivatives of the formula I have to an outstanding degree the properties of protecting cultivated plants against the damaging effects of herbicidally active 2-[4-(5-chloro-3-fluoropyridin-2-yloxy)-phenoxy]-propionic acid derivatives. The aforementioned herbicidal active substances are known from the published European Patent Applications Nos. EP-A-83556 and EP-A-97460, and can be produced by the methods described therein. 2-[4-(5-Chloro-3-fluoropyridin-2-yloxy)-phenoxy]-propionic acid derivatives which are particularly effective and which are applicable according to the teaching of the present invention correspond to the formula II

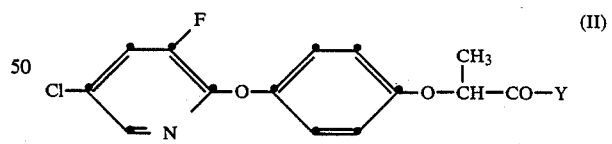

wherein
Y is a group —NR¹⁶R¹⁷, —O—R¹⁸, —S—R¹⁸ or —O—N=CR¹⁹R²⁰,

R¹⁶ and R¹⁷ independently of one another are each hydrogen, C₁–C₈-alkoxy, C₁–C₈-alkyl, phenyl or benzyl, R¹⁶ and R¹⁷ together with nitrogen atom carrying them form a 5- or 6-membered saturated nitrogen heterocycle which can be interrupted by an oxygen or sulfur atom, R¹⁸ is hydrogen or the equivalent of an alkali metal, alkaline-earth metal, copper or iron ion; or is a quaternary C₁–C₄-alkylammonium or C₁–C₄-hydroxyalkylammonium radical; a C₁–C₉-alkyl radical which is unsubstituted or mono- or polysubstituted by amino, halogen, hydroxyl, cyano, nitro, phenyl, $C_1$-$C_4$-alkoxy, polyethoxy having 2 to 6 ethylene oxide units, —$COOR^{21}$, —$COSR^{21}$, —$CONH_2$—, —$CON(C_1$-$C_4$-alkoxy)-$C_1$-$C_4$-alkyl, —CO—N—di-$C_1$-$C_4$-alkyl, —CONH—$C_1$-$C_4$-alkyl, —$N(C_1$-$C_4$-alkoxy)-$C_1$-$C_4$-alkyl or di-$C_1$-$C_4$-alkylamino; or is a $C_3$-$C_9$-alkenyl radical which is unsubsituted or substituted by halogen or $C_1$-$C_4$-alkoxy; or is a $C_3$-$C_9$-alkynyl radical which is unsubstituted or substituted by halogen or $C_1$-$C_4$-alkoxy; or is $C_3$-$C_9$-cycloalkyl; or phenyl which is unsubstituted or substituted by cyano, $C_1$-$C_4$-alkyl, $C_1$-$C_4$-alkoxy, acetyl, —$COOR^{21}$, $COSR^{21}$, —$CONH_2$, —$CON(C_1$-$C_4$-alkoxy)-$C_1$-$C_4$-alkyl, —CO—N—di-$C_1$-$C_4$-alkyl or —CONH-$C_1$-$C_4$-alkyl, $R^{19}$ and $R^{20}$ independently of one another are each $C_1$-$C_4$-alkyl, or together form a 3- to 6-membered alkylene chain, and $R^{21}$ is hydrogen, $C_1$-$C_6$-alkyl, $C_1$-$C_6$-haloalkyl, $C_2$-$C_6$-alkoxyalkyl, $C_3$-$C_6$-alkenyl, $C_3$-$C_6$-haloalkenyl, $C_3$-$C_6$-alkynyl or $C_3$-$C_6$-haloalkynyl.

In the compounds of the formula II, halogen, as an indenpendent substituent, or as part of another substituent, such as haloalkyl, haloalkoxy, haloalkenyl or haloalkynyl, is fluorine, chlorine, bromine or iodine, with fluorine or chlorine being preferred.

Depending on the number of carbon atoms present, alkyl is methyl, ethyl, n-propyl or i-propyl, as well as the isomeric butyl, pentyl, hexyl, heptyl or octyl. The alkyl groups contained in the radicals alkoxy, alkoxyalkyl, haloalkyl or haloalkoxy have the same meanings. Alkyl groups having a low number of carbon atoms are preferred in each case. haloalkyl radicals, are: fluoromethyl, difluoromethyl, trifluoromethyl, chloromethyl, trichloromethyl, 2-fluoroethyl, 2,2,2-trifluoroethyl, 1,1,2,2-tetrafluoroethyl, perfluoroethyl, 2-chloroethyl, 2,2,2-trichloroethyl, 2-bromoethyl and 1,1,2,3,3,3-hexafluoropropyl.

Cycloalkyl denotes mono- and bi-cyclic saturated hydrocarbon ring systems, such as cyclopropyl, cyclobutyl, cyclopentyl, cyclohexyl, cycloheptyl, cyclooctyl, cyclononyl, bicyclo[4.3.0]nonyl, bicyclo[5.2.0]nonyl or bicyclo[2.2.2]octyl.

Particularly remarkable is the protective action of quinoline derivatives of the formula I against such herbicides of the formula II in which Y is the group —O—$R^{18}$, —S—$R^{18}$ or —O—N═$CR^{19}R^{20}$, wherein $R^{18}$ is hydrogen, $C_1$-$C_4$-alkyl or $C_3$-$C_4$-alkynyl, or $C_1$-$C_4$-alkyl which is substituted by $C_1$-$C_4$-alkoxycarbonyl or di-$C_1$-$C_4$-alkylamino, and $R^{19}$ and $R^{20}$ independently of one another are each $C_1$-$C_4$-alkyl, or $R^{19}$ and $R^{20}$ together form a $C_4$-$C_7$-alkylene chain.

Individual meanings for Y to be especially emphasised are: methoxy, ethoxy, propyloxy, isopropyloxy, butyloxy, dimethylaminoethoxy, propargyloxy, 1-cyano-1-methylethoxy, methoxycarbonylmethylthio, 1-ethoxycarbonylethoxy, butyloxycarbonyl, —O—N═$C(CH_3)_2$, —O—N═$C(CH_3)C_2H_5$ or —O—N═$C(CH_2)_5$.

The optically active carbon atom of the propionic acid group usually has both the R- and S-configuration. Except where otherwise specially stated, the racemic mixtures are meant herein. Preferred herbicides of the formula II have the the 2R configuration.

Examples of herbicidally active 2-[4-(5-chloro-3-fluoropyridin-2-yloxy)-phenoxy]-propionic acid derivatives, against the action of which cultivated plants can be protected according to the invention, are listed in the following Table 2.

TABLE 2

(II)

[Structure: Cl-substituted pyridine with F, linked via O to phenyl ring, linked via O—CH(CH₃)—CO—Y]

| No. | Y | Physical constants |
|---|---|---|
| 2.1 | —$OCH_3$ | m.p. 63–64° C. |
| 2.2 | —$OC_4H_9$—n | $n_D^{35}$ = 1.5275 |
| 2.3 | —O—N═$C(CH_3)_2$ | $n_D^{35}$ = 1.5488 |
| 2.4 | —$OC_2H_5$ | $n_D^{35}$ = 1.5358 |
| 2.5 | —O—$CH_2$—$CH_2$—$N(CH_3)_2$ | $n_D^{35}$ = 1.5334 |
| 2.6 | —O—$CH_2$—C≡CH | $n_D^{35}$ = 1.5492 |
| 2.7 | —O—C(CH₃)₂—CN | $n_D^{35}$ = 1.5330 |
| 2.8 | —S—$CH_2$—$COOCH_3$ | $n_D^{35}$ = 1.5607 |
| 2.9 | —O—CH(CH₃)—$COOC_2H_5$ | $n_D^{35}$ = 1.5227 |
| 2.10 | —O—$CH_2$—$COOC_4H_9$—n | $n_D^{35}$ = 1.5223 |
| 2.11 | —$OC_3H_7$—n | $n_D^{35}$ = 1.5319 |
| 2.12 | —$OC_3H_7$—i | $n_D^{35}$ = 1.5284 |
| 2.13 | —O—N═C(CH₃)—$C_2H_5$ | $n_D^{35}$ = 1.5340 |
| 2.14 | —O—N═C (cyclohexylidene) | $n_D^{35}$ = 1.5360 |
| 2.15 | —$OCH_3$ (2R) | $n_D^{35}$ = 1.5359 |
| 2.16 | —OH | m.p. 95–97° C. |
| 2.17 | —S—$CH_2$—$COOCH_3$ (2R) | $n_D^{35}$ = 1.5623 |
| 2.18 | —O—CH(CH₃)—$COOC_2H_5$ (2R,S) | $n_D^{35}$ = 1,5223 |
| 2.19 | —O—$CH_2$—C≡CH (2R) | m.p. 55–56° C. |
| 2.20 | —NH—$OCH_3$ | m.p. 103–105° C. |

Cultivated plants which can be protected by quinoline derivatives of the formula I against the harmful effects of herbicides of the formula II are in particular those which are of importance in the foodstuffs and textile fields, for example sugar cane and especially cultivated millet, maize, rice and other varieties of cereals (wheat, rye, barley and oats). The application in wheat, rye, barley and rice crops is at this point to be particularly emphasised.

A preferred embodiment of the process according to the invention comprises the use of:
2-quinolin-8-yloxy-acetic acid isopropyl ester,
2-(5-chloroquinolin-8-yloxy)-acetic acid-n-dodecyl ester,
2-(5-chloroquinolin-8-yloxy)-acetic acid-n-butyl ester,
2-(5-chloroquinolin-8-yloxy)-acetic acid-n-octyl ester,
2-quinolin-8-yloxy-acetic acid-s-butyl ester,
2-(5-chloroquinolin-8-yloxy)-thioacetic acid-n-octyl ester,
2-(5-chloroquinolin-8-yloxy)-acetic acid-(2-butenyl) ester, 2-(5-chloroquinolin-8-yloxy)-acetic acid methallyl ester,
2-(5-chloroquinolin-8-yloxy)-acetic acid-(2-isopropyloxyethyl) ester,
2-(5-chloroquinolin-8-yloxy)-acetic acid-(2-phenoxyethyl) ester,
2-(5-chloroquinolin-8-yloxy)-acetic acid-(1-methylbutyl) ester,
2-(5-chloroquinolin-8-yloxy)-acetic acid cyclohexyl ester,
2-(5-chloroquinolin-8-yloxy)-acetic acid-s-butyl ester,
2-(5-chloroquinolin-8-yloxy)-acetic acid-(2-methylpentyl) ester,
2-(5-chloroquinolin-8-yloxy)-thioacetic acid-n-butyl ester,
2-(5-chloroquinolin-8-yloxy)-acetic acid-(3,6-dioxadecyl) ester,
2-(5-chloroquinolin-8-yloxy)-acetic acid-(3-methoxybutyl) ester,
2-(5-chloroquinolin-8-yloxy)-acetic acid-(1-ethylbutyl) ester,
2-(5-chloroquinolin-8-yloxy)-acetic acid-(2-ethylbutyl) ester,
2-(5-chloroquinolin-8-yloxy)-acetic acid-(1-methylisopentyl) ester,
2-(5-chloroquinolin-8-yloxy)-acetic acid-n-undecyl ester,
2-(5-chloroquinolin-8-yloxy)-acetic acid-(2-methylbutyl) ester,
2-(5-chloroquinolin-8-yloxy)-thioacetic acid-s-butyl ester,
2-(5-chloroquinolin-8-yloxy)-acetic acid-(3,6-dioxaheptyl) ester,
2-(5-chloroquinolin-8-yloxy)-acetic acid-n-heptyl ester,
2-(5-chloroquinolin-8-yloxy)-thioacetic acid-n-dodecyl ester,
2-(5-chloroquinolin-8-yloxy)-thioacetic acid-n-decyl ester,
2-(5-chloroquinolin-8-yloxy)-acetic acid-(1-propylpropargyl) ester,
2-(5-chloroquinolin-8-yloxy)-acetic acid-(1-methylisobutyl) ester,
2-(5-chloroquinolin-8-yloxy)-thioacetic acid-tert-butyl ester,
2-(5-chloroquinolin-8-yloxy)-acetic acid-neopentyl ester,
2-(5-chloroquinolin-8-yloxy)-thioacetic acid-n-propyl ester,
2-(5-chloroquinolin-8-yloxy)-acetic acid-(1-methylhexyl) ester,
2-(5-chloroquinolin-8-yloxy)-thioacetic acid ethyl ester,
2-(5-chloroquinolin-8-yloxy)-acetic acid-(2-ethylhexyl) ester,
2-(5-chloroquinolin-8-yloxy)-thioacetic acid-i-butyl ester,
2-quinolin-8-yloxy-thioacetic acid-n-decyl ester,
2-(5-chloroquinolin-8-yloxy)-acetic acid-i-pentyl ester,
2-(5-chloroquinolin-8-yloxy)-acetic acid-(1-ethylpentyl) ester,
2-(5-chloroquinolin-8-yloxy)-acetic acid-(1-propylbutyl) ester,
2-(5-chloroquinolin-8-yloxy)-thioacetic acid-n-hexyl ester,
2-(5-chloroquinolin-8-yloxy)-acetic acid-n-hexyl ester,
2-(5-chloroquinolin-8-yloxy)-thioacetic acid-i-propyl ester,
2-(5-chloroquinolin-8-yloxy)-acetic acid -(1-pentylallyl) ester,
2-(5-chloroquinolin-8-yloxy)-acetic acid-(1-methylpentyl) ester,
2-(5-chloroquinolin-8-yloxy)-acetic acid-(1,1-dimethylpropargyl) ester,
2-(5-chloroquinolin-8-yloxy)-acetic acid-(1-ethyl-1-methylpropargyl) ester,
2-(5-chloroquinolin-8-yloxy)-acetic acid-n-butyloxycarbonylmethyl ester,
2-(5-chloroquinolin-8-yloxy)-acetic acid-(1-n-butyloxycarbonylethyl) ester,
2-(5-chloroquinolin-8-yloxy)-acetic acid-(1-methylisohexyl) ester,
2-(5-chloroquinolin-8-yloxy)-acetic acid-(1-phenylisobutyl) ester,
2-(5-chloroquinolin-8-yloxy)-acetic acid-[1-methyl-2-(2-methylphenoxy)-ethyl]ester,
2-(5-chloroquinolin-8-yloxy)-acetic acid-(1-phenylethyl) ester,
2-(5-chloroquinolin-8-yloxy)-acetic acid-[1-methyl-2-(4-ethylphenoxy)-ethyl]ester,
2-(5-chloroquinolin-8-yloxy)-acetic acid-(1-methyl-2-phenylethyl) ester,
2-(5-chloroquinolin-8-yloxy)-acetic acid-[1-methyl-2-(2-isopropylphenoxy)-ethyl]ester,
2-(5-chloroquinolin-8-yloxy)-acetic acid-(1-phenylpropyl) ester,
2-(5-chloroquinolin-8-yloxy)-acetic acid-[1-methyl-2-(2-ethylphenoxy)-ethyl]ester,
2-(5-chloroquinolin-8-yloxy)-acetic acid-[1-methyl-2-(3-ethylphenoxy)-ethyl]ester,
2-(5-chloroquinolin-8-yloxy)-acetic acid-(1-methyl-2-phenoxyethyl) ester,
2-(5-chloroquinolin-8-yloxy)-acetic acid-(1-methyl-3-phenylpropyl) ester,
2-(5-chloroquinolin-8-yloxy)-acetic acid-[1-methyl-2-(3-methylphenoxy)-ethyl]ester,
2-(5-chloroquinolin-8-yloxy)-acetic acid-[1-methyl-2-(4-isopropylphenoxy)-ethyl]ester or
2-(5-chloroquinolin-8-yloxy)-acetic acid-[1-methyl-2-(4-methylphenoxy)-ethyl]ester for the protection of cultivated plants, particularly cereals, against the damaging action of 2-[4-(5-chloro-3-fluoropyridin-2-yloxy)-phenoxy]-propionic acid methyl ester, 2-[4-(5-chloro-3-fluoropyridin-2-yloxy)-phenoxy]-propionic acid propargyl ester, 2-[4-(5-chloro-3-fluoropyridin-2-yloxy)-phenoxy]-thiopropionic acid-S-methoxycarbonylmethyl ester or 2-[4-(5-chloro-3-fluoropyridin-2-yloxy)-phenoxy]propionic acid-(1-ethoxycarbonylethyl) ester.

By virtue of the excellent results obtainable, the user will preferably apply the compound
2-(5-chloroquinolin-8-yloxy)-acetic acid methallyl ester,
2-(5-chloroquinolin-8-yloxy)-acetic acid-(2-phenoxyethyl) ester,
2-(5-chloroquinolin-8-yloxy)-acetic acid-(1-methylbutyl) ester,
2-(5-chloroquinolin-8-yloxy)-acetic acid-(1-ethylbutyl) ester,
2-(5-chloroquinolin-8-yloxy)-acetic acid-(1-methylisopentyl) ester,
2-(5-chloroquinolin-8-yloxy)-acetic acid-(1-methylhexyl) ester,
2-(5-chloroquinolin-8-yloxy)-acetic acid-(1-ethylpentyl) ester,
2-(5-chloroquinolin-8-yloxy)-acetic acid-(1-propylbutyl) ester, 2-(5-chloroquinolin-8-yloxy)-acetic acid-(1-pentylallyl) ester,
2-(5-chloroquinolin-8-yloxy)-acetic acid-(1-methylpentyl) ester,
2-(5-chloroquinolin-8-yloxy)-acetic acid-(1-methylisohexyl) ester,
2-(5-chloroquinolin-8-yloxy)-acetic acid-(1-phenylisobutyl) ester,
2-(5-chloroquinolin-8-yloxy)-acetic acid-(1-phenylethyl) ester,
2-(5-chloroquinolin-8-yloxy)-acetic acid-[1-methyl-2-(4-ethylphenoxy)-ethyl]ester,
2-(5-chloroquinolin-8-yloxy)-acetic acid-(1-methyl-2-phenylethyl) ester,
2-(5-chloroquinolin-8-yloxy)-acetic acid-(1-phenylpropyl) ester,
2-(5-chloroquinolin-8-yloxy)-acetic acid-(1-methyl-2-phenoxyethyl) ester,
2-(5-chloroquinolin-8-yloxy)-acetic acid-(1-methyl-3-phenylpropyl) ester or
2-(5-chloroquinolin-8-yloxy)-acetic acid-[1-methyl-2-(4-methylphenoxy)-ethyl]ester
for the protection of cultivated plants, especially cereals, against the harmful action of 2-[4-(5-chloro-3-fluoropyridin-2-yloxy)-phenoxy]-propionic acid methyl ester, 2-[4-(5-chloro-3-fluoropyridin-2-yloxy)-phenoxy]-propionic acid propargyl ester, 2-[4-(5-chloro-3-fluoropyridin-2-yloxy)-phenoxy]-thiopropionic acid-S-methoxycarbonylmethyl ester or 2-[4-(5-chloro-3-fluoropyridin-2-yloxy)-phenoxy]propionic acid-(1-ethoxycarbonylethyl) ester.

A suitable process for protecting cultivated plants by the use of compounds of the formula I comprises treating cultivated plants, parts of these plants, or soils intended for the cultivation of the cultivated plants, before or after introduction of the vegetable material into the soil, with a compound of the formula I or with a composition containing such a compound. The treatment can be carried out before, simultaneously with or after the application of the herbicide of the formula II. Parts of plants concerned are especially those which are capable of the new formation of a plant, for example seeds, fruits, stem parts and branches (cuttings), as well as roots, tubers and rhizomes.

The invention relates also to a process for the selective control of weeds in crops of cultivated plants, in which process the cultivated plants, parts of the cultivated plants, or cultivated areas for cultivated plants are treated with a herbicide of the formula II and a compound of the formula I, or with a composition containing a combination of such a herbicide and a compound of the formula I.

The present invention relates also to herbicidal compositions containing a combination of the antagonistic component I and the herbicidal component II.

Such compositions preferably contain, as the antagonistic component, a compound selected from the series comprising:
2-quinolin-8-yloxy-acetic acid isopropyl ester,
2-(5-chloroquinolin-8-yloxy)-acetic acid-n-dodecyl ester,
2-(5-chloroquinolin-8-yloxy)-acetic acid-n-butyl ester,
2-(5-chloroquinolin-8-yloxy)-acetic acid-n-octyl ester,
2-quinolin-8-yloxy-acetic acid-s-butyl ester,
2-(5-chloroquinolin-8-yloxy)-thioacetic acid-n-octyl ester,
2-(5-chloroquinolin-8-yloxy)-acetic acid-(2-butenyl) ester,
2-(5-chloroquinolin-8-yloxy)-acetic acid methallyl ester,
2-(5-chloroquinolin-8-yloxy)-acetic acid-(2-isopropyloxyethyl) ester,
2-(5-chloroquinolin-8-yloxy)-acetic acid-(2-phenoxyethyl) ester
2-(5-chloroquinolin-8-yloxy)-acetic acid-(1-methylbutyl) ester,
2-(5-chloroquinolin-8-yloxy)-acetic acid cyclohexyl ester,
2-(5-chloroquinolin-8-yloxy)-acetic acid-s-butyl ester,
2-(5-chloroquinolin-8-yloxy)-acetic acid-(2-methylpentyl) ester,
2-(5-chloroquinolin-8-yloxy)-thioacetic acid-n-butyl ester,
2-(5-chloroquinolin-8-yloxy)-acetic acid-(3,6-dioxadecyl) ester,
2-(5-chloroquinolin-8-yloxy)-acetic acid-(3-methoxybutyl) ester,
2-(5-chloroquinolin-8-yloxy)-acetic acid-(1-ethylbutyl) ester,
2-(5-chloroquinolin-8-yloxy)-acetic acid-(2-ethylbutyl) ester,
2-(5-chloroquinolin-8-yloxy)-acetic acid-(1-methylisopentyl) ester,
2-(5-chloroquinolin-8-yloxy)-acetic acid-n-undecyl ester,
2-(5-chloroquinolin-8-yloxy)-acetic acid-(2-methylbutyl) ester,
2-(5-chloroquinolin-8-yloxy)-thioacetic acid-s-butyl ester,
2-(5-chloroquinolin-8-yloxy)-acetic acid-(3,6-dioxaheptyl) ester,
2-(5-chloroquinolin-8-yloxy)-acetic acid-n-heptyl ester,
2-(5-chloroquinolin-8-yloxy)-thioacetic acid-n-dodecyl ester,
2-(5-chloroquinolin-8-yloxy)-thioacetic acid-n-decyl ester,
2-(5-chloroquinolin-8-yloxy)-acetic acid-(1-propylpropargyl) ester,
2-(5-chloroquinolin-8-yloxy)-acetic acid-(1-methylisobutyl) ester,
2-(5-chloroquinolin-8-yloxy)-thioacetic acid-tert-butyl ester,
2-(5-chloroquinolin-8-yloxy)-acetic acid-neopentyl ester,
2-(5-chloroquinolin-8-yloxy)-thioacetic acid-n-propyl ester,
2-(5-chloroquinolin-8-yloxy)-acetic acid-(1-methylhexyl) ester
2-(5-chloroquinolin-8-yloxy)-thioacetic acid ethyl ester,
2-(5-chloroquinolin-8-yloxy)-acetic acid-(2-ethylhexyl) ester,
2-(5-chloroquinolin-8-yloxy)-thioacetic acid-i-butyl ester,
2-quinolin-8-yloxy-thioacetic acid-n-decyl ester,
2-(5-chloroquinolin-8-yloxy)-acetic acid-i-pentyl ester,
2-(5-chloroquinolin-8-yloxy)-acetic acid-(1-ethylpentyl) ester,
2-(5-chloroquinolin-8-yloxy)-acetic acid-(1-propylbutyl) ester,
2-(5-chloroquinolin-8-yloxy)-thioacetic acid-n-hexyl ester,
2-(5-chloroquinolin-8-yloxy)-acetic acid-n-hexyl ester,
2-(5-chloroquinolin-8-yloxy)-thioacetic acid-i-propyl ester,
2-(5-chloroquinolin-8-yloxy)-acetic acid-(1-pentylallyl) ester, 2-(5-chloroquinolin-8-yloxy)-acetic acid-(1-methylpentyl) ester,
2-(5-chloroquinolin-8-yloxy)-acetic acid-(1,1-dimethylpropargyl) ester,
2-(5-chloroquinolin-8-yloxy)-acetic acid-(1-ethyl-1-methylpropargyl) ester,
2-(5-chloroquinolin-8-yloxy)-acetic acid-n-butyloxycarbonylmethyl ester,
2-(5-chloroquinolin-8-yloxy)-acetic acid-(1-n-butyloxycarbonylethyl) ester,
2-(5-chloroquinolin-8-yloxy)-acetic acid-(1-methylisohexyl) ester,
2-(5-chloroquinolin-8-yloxy)-acetic acid-(1-phenylisobutyl) ester,
2-(5-chloroquinolin-8-yloxy)-acetic acid-[1-methyl-2-(2-methylphenoxy)-ethyl]ester,
2-(5-chloroquinolin-8-yloxy)-acetic acid-(1-phenylethyl) ester,
2-(5-chloroquinolin-8-yloxy)-acetic acid-[1-methyl-2-(4-ethylphenoxy)-ethyl]ester,
2-(5-chloroquinolin-8-yloxy)-acetic acid-(1-methyl-2-phenylethyl) ester,
2-(5-chloroquinolin-8-yloxy)-acetic acid-[1-methyl-2-(2-isopropylphenoxy)-ethyl]ester,
2-(5-chloroquinolin-8-yloxy)-acetic acid-(1-phenylpropyl) ester,
2-(5-chloroquinolin-8-yloxy)-acetic acid-[1-methyl-2-(2-ethylphenoxy)-ethyl]ester,
2-(5-chloroquinolin-8-yloxy)-acetic acid-[1-methyl-2-(3-ethylphenoxy)-ethyl]ester,
2-(5-chloroquinolin-8-yloxy)-acetic acid-(1-methyl-2-phenoxyethyl) ester,
2-(5-chloroquinolin-8-yloxy)-acetic acid-(1-methyl-3-phenylpropyl) ester,
2-(5-chloroquinolin-8-yloxy)-acetic acid-[1-methyl-2-(3-methylphenoxy)-ethyl]ester,
2-(5-chloroquinolin-8-yloxy)-acetic acid-[1-methyl-2-(4-isopropylphenoxy)-ethyl]ester and
2-(5-chloroquinolin-8-yloxy)-acetic acid-[1-methyl-2-(4-methylphenoxy)-ethyl]ester,
and, as the herbicidal component, a compound selected from the series comprising: 2-[4-(5-chloro-3-fluoropyridin-2-yloxy)-phenoxy]-propionic acid methyl ester, 2-[4-(5-chloro-3-fluoropyridin-2-yloxy)-phenoxy]-propionic acid propargyl ester, 2-[4-(5-chloro-3-fluoropyridin-2-yloxy)-phenoxy]-thiopropionic acid-S-methoxycarbonylmethyl ester or 2-[4-(5-chloro-3-fluoropyridin-2-yloxy)phenoxy]-propionic acid-(1-ethoxycarbonylethyl) ester.

Particularly preferred among these compositions are those which contain, as the antagonistic component, the compound:
2-(5-chloroquinolin-8-yloxy)-acetic acid methallyl ester,
2-(5-chloroquinolin-8-yloxy)-acetic acid-(2-phenoxyethyl) ester,
2-(5-chloroquinolin-8-yloxy)-acetic acid-(1-methylbutyl) ester,
2-(5-chloroquinolin-8-yloxy)-acetic acid-(1-ethylbutyl) ester,
2-(5-chloroquinolin-8-yloxy)-acetic acid-(1-methylisopentyl) ester,
2-(5-chloroquinolin-8-yloxy)-acetic acid-(1-methylhexyl) ester,
2-(5-chloroquinolin-8-yloxy)-acetic acid-(1-ethylpentyl) ester,
2-(5-chloroquinolin-8-yloxy)-acetic acid-(1-propylbutyl) ester,
2-(5-chloroquinolin-8-yloxy)-acetic acid-(1-pentylallyl) ester,
2-(5-chloroquinolin-8-yloxy)-acetic acid-(1-methylpentyl) ester,
2-(5-chloroquinolin-8-yloxy)-acetic acid-(1-methylisohexyl) ester,
2-(5-chloroquinolin-8-yloxy)-acetic acid-(1-phenylisobutyl) ester,
2-(5-chloroquinolin-8-yloxy)-acetic acid-(1-phenylethyl) ester,
2-(5-chloroquinolin-8-yloxy)-acetic acid-[1-methyl-2-(4-ethylphenoxy)-ethyl]ester,
2-(5-chloroquinolin-8-yloxy)-acetic acid-(1-methyl-2-phenylethyl) ester,
2-(5-chloroquinolin-8-yloxy)-acetic acid-(1-phenylpropyl) ester,
2-(5-chloroquinolin-8-yloxy)-acetic acid-(1-methyl-2-phenoxyethyl) ester,
2-(5-chloroquinolin-8-yloxy)-acetic acid-(1-methyl-3-phenylpropyl) ester or
2-(5-chloroquinolin-8-yloxy)-acetic acid-[1-methyl-2-(4-methylphenoxy)-ethyl]ester,
and as the herbicidal component the compound: 2-[4-chloro-3-fluoropyridin-2-yloxy)-phenoxy]-propionic acid methyl ester, 2-[4-(5-chloro-3-fluoropyridin-2-yloxy)phenoxy]-propionic acid propargyl ester, 2-[4-(5-chloro-3-fluoropyridin-2-yloxy)-phenoxy]-thiopropionic acid-S-methoxycarbonylmethyl ester or 2-[4-(5-chloro-3-fluoropyridin-2-yloxy)-phenoxy]-propionic acid-(1-ethoxycarbonylethyl) ester.

Of these compositions, preference is given moreover to those which contain as the antagonistic active ingredient:
2-(5-chloroquinolin-8-yloxy)-acetic acid methallyl ester,
2-(5-chloroquinolin-8-yloxy)-acetic acid-(2-phenoxyethyl) ester,
2-(5-chloroquinolin-8-yloxy)-acetic acid-(1-methylisopentyl) ester or
2-(5-chloroquinolin-8-yloxy)-acetic acid-(1-methylhexyl) ester.

The weeds to be controlled can be both monocotyledonous and dicotyledonous.

Cultivated plants or parts of these plants to be protected are for example those mentioned in the foregoing. The cultivated areas concerned are those on which cultivated plants are already growing, or on which the seed of these plants has been sown, and also the soil intended for the growing of these cultivated plants.

The amount of antidote to be applied in proportion to the amount of herbicide depends largely upon the type of application. In the case of a field treatment, which is carried out either with the use of a tank mixture containing a combination of antidote and herbicide, or with a separate application of antidote and herbicide, the employed ratio of antidote to herbicide is as a rule from 1:100 to 10:1, preferably 1:20 to 1:1, and particularly 1:1. With seed dressing, however, the amounts of antidote required in proportion to the amounts of herbicide applied per hectare of cultivated land are much smaller From the field treatment, 0.01 to 10 kg of antidote per hectare, preferably 0.05 to 0.5 kg of antidote per hectare, are as a rule applied. For seed dressing, there are generally used 0.01 to 10 g of antidote per kg of seed, preferably 0.05 to 2 g of antidote per kg of seed. When the antidote is applied in liquid form by seed soaking shortly before sowing, there are advantageously employed antidote solutions containing the active ingredient at a concentration of 1 to 10,000 ppm, preferably 100 to 1000 ppm.

For application, the compounds of the formula I, or combinations of compounds of the formula I with the herbicides to be antagonised, are advantageously used together with the auxiliaries customarily employed in formulation practice, and are thus processed, in a known manner, for example into the form of emulsion concentrates, brushable pastes, directly sprayable or dilutable solutions, diluted emulsions, wettable powders, soluble powders, dusts or granulates, and also encapsulations in for example polymeric substances. The application processes, such as spraying, atomising, dusting, scattering, brushing or pouring, and likewise the type of compositions to be used, are selected to suit the objectives to be achieved and the given conditions.

The formulations, that is to say, the compositions or preparations containing the active ingredient of the formula I, or a combination of active ingredient of the formula I and the herbicide to be antagonised, and optionally a solid or liquid additive, are produced in a known manner, for example by the intimate mixing and/or grinding of the active ingredients with extenders, such as with solvents, solid carriers and optionally surface active compounds (tensides).

Suitable solvents are: aromatic hydrocarbons, preferably the fractions $C_8$ to $C_{12}$, such as xylene mixtures or substituted naphthalenes, phthalic esters, such as dibutyl- or dioctylphthalate, aliphatic hydrocarbons, such as cyclohexane or paraffins, alcohols and glycols, as well as ethers and esters thereof, such as ethanol, ethylene glycol, ethylene glycol monomethyl or -ethyl ethers, ketones, such as cyclohexanone, strongly polar solvents, such as N-methyl-2-pyrrolidone, dimethyl sulfoxide or dimethylformamide, as well as optionally epoxidised vegetable oils, such as epoxidised coconut oil or soybean oil; or water.

The solid carriers used, for example for dusts and dispersible powers, are as a rule natural mineral fillers, such as calcite, talcum, kaolin, montmorillonite or attapulgite. In order to improve the physical properties, it is also possible to add highly dispersed silicic acid or highly dispersed absorbent polymers. Suitable granulated adsorptive carriers are porous types, for example pumice, ground brick, sepiolite or bentonite; and suitable nonsorbent carriers are materials such as calcite or sand. There can also be used a great number of pregranulated materials of inorganic or organic nature, such as in particular dolomite or ground plant residues.

Suitable surface-active compounds are, depending on the nature of the active ingredient of the formula I to be formulated, and optionally also of the herbicide to be antagonised, nonionic, cationic and/or anionic tensides having good emulsifying, dispersing and wetting properties. By 'tensides' are also meant mixtures of tensides.

Suitable anionic tensides are both so-called water-soluble soaps as well as water-soluble, synthetic, surface-active compounds.

Soaps which are applicable are the alkali metal, alkaline-earth metal or optionally substituted ammonium salts of higher fatty acids ($C_{10}$–$C_{22}$), for example the Na or K salts of oleic or stearic acid, or of natural fatty acid mixtures, which can be obtained for example from coconut oil or tallow oil. Also to be mentioned are the fatty acid-methyl-taurine salts.

So-called synthetic tensides are however more frequently used, particularly fatty sulfonates, fatty sulfates, sulfonated benzimidazole derivatives or alkylarylsulfonates. The fatty sulfonates or sulfates are as a rule in the form of alkali metal, alkaline-earth metal or optionally substituted ammonium salts, and contain an alkyl group having 8 to 22 C atoms, 'alkyl' including also the alkyl moiety of acyl groups, for example the Na or Ca salt of ligninsulfonic acid, of dodecylsulfuric acid ester or of a fatty alcohol sulfate mixture produced from natural fatty acids. Included among these are also the salts of sulfuric acid esters and sulfonic acids of fatty alcohol ethylene oxide adducts. The sulfonated benzimidazole derivatives preferably contain 2 sulfonic acid groups and a fatty acid group having 8–22 C atoms. Alkylarylsulfonates are for example the Na, Ca or triethanolamine salts of dodecylbenzenesulfonic acid, of dibutylnaphthalenesulfonic acid or of a naphthalenesulfonic acid-formaldehyde condensation product. Also suitable are corresponding phosphates, for example salts of the phosphoric ester of a p-nonylphenol-(4–14)-ethylene oxide adduct, or phospholipides.

Suitable nonionic tensides are in particular polyglycol ether derivatives of aliphatic or cycloaliphatic alcohols, saturated or unsaturated fatty acids and alkylphenols, which can contain 3 to 30 glycol ether groups and 8 to 20 carbon atoms in the (aliphatic) hydrocarbon radical and 6 to 18 carbon atoms in the alkyl moiety of the alkylphenols.

Further suitable nonionic tensides are the water-soluble polyethylene oxide adducts, which contain 20 to 250 ethylene glycol ether groups and 10 to 100 propylene glycol ether groups, with polypropylene glycol, ethylenediaminopolypropylene glycol and alkylpolypropylene glycol having 1 to 10 carbon atoms in the alkyl chain. The compounds mentioned usually contain 1 to 5 ethylene glycol units per propylene glycol unit. Examples of nonionic tensides which may be mentioned are: nonylphenolpolyethoxyethanols, castor oil polyglycol ethers, polypropylene/polyethylene oxide adducts, tributylphenoxypolyethoxyethanol, polyethylene glycol and octylphenoxypolyethoxyethanol. Suitable also are fatty acid esters of polyoxyethylenesorbitan, such as polyoxyethylenesorbitan-trioleate.

In the case of the cationic tensides, they are in particular quaternary ammonium salts which contain as N-substituents as least one alkyl group having 8 to 22 C atoms and, as further substituents, lower, optionally halogenated alkyl, benzyl or lower hydroxyalkyl groups. The salts are preferably in the form of halides, methyl sulfates or ethyl sulfates, for example stearyltrimethylammonium chloride or benzyldi(2-chloroethyl)ethylammonium bromide.

The tensides customarily used in formulation practice are described, inter alia, in the following publications:

"Mc Cutcheon's Detergents and Emulsifiers Annual", MC Publishing Corp., Ridgewood, N.J., 1981, and Stache, H., "Tensid-Taschenbuch", Carl Henser Verlag, Munich/Vienna, 1981.

The agrochemical preparations contain as a rule 0.1 to 99% by weight, especially 0.1 to 95% by weight of active ingredient of the formula I or of an active-ingredient mixture of antidote and herbicide, 1 to 99.9% by weight, particularly 5 99.8% by weight, of a solid or liquid additive, and 0 to 25% by weight, especially 0.1 to 25% by weight, of a tenside.

Whereas commercial products are preferably in the form of concentrated compositions, the preparations employed by the end-user are as a rule diluted.

The compositions can also contain further additives, such as stabilisers, antifoaming agents, viscosity regulators, binders and adhesives, as well as fertilisers or other active substances for obtaining special effects.

For use of compounds of the formula I, or of compositions containing them, for the protection of cultivated plants against the harmful effects of herbicides of the formula II, various methods and techniques are applicable, such as those described in the following.

(i) Seed dressing (a) Dressing of the seeds with an active ingredient of the formula I, formulated as a wettable powder, by shaking in a vessel until there is a uniform distribution over the surface of the seeds (dry dressing). The amount of active ingredient of the formula I used for this purpose is about 1 to 500 g (4 g to 2 kg of wettable powder) per 100 kg of seed.

(b) Dressing of the seeds with an emulsion concentrate of the active ingredient of the formula I according to method (a) (wet dressing).

(c) Dressing by immersion of the seed in a liquor containing 50–3200 ppm of active ingredient of the formula I for 1 to 72 hours, and optionally subsequent drying of the seed (immersion dressing).

The dressing of the seed or the treatment of the germinated young seedlings is, in accordance with nature, the preferred method of application, because the treatment with the active ingredient is directed completely at the target growth. There are used as a rule 1 g to 500 g, preferably 5 to 250 g, of antidote per 100 kg of seed; however, depending on the method of treatment, which may render possible also the addition of other active substances or micronutrients, the stated limiting concentrations may be varied upwards or downwards (repeat dressing).

(ii) Application as tank mixture

A liquid preparation of a mixture of antidote and herbicide (quantitative ratio between 10:1 and 1:100) is used, the applied amount of herbicide being 0.1 to 10 kg per hectare. This tank mixture is preferably applied before or immediately after sowing.

(iii) Application into the seed furrow

The antidote is introduced, as an emulsion concentrate, wettable powder or granulate, into the open seed furrow, and, after the covering of the seed furrow in the normal manner, the herbicide is applied before the emergence of the plants.

(iv) Controlled release of active ingredient

The active ingredient of the formula I is absorbed, in solution, onto mineral granular carriers or polymerised granulates (urea/formaldehyde), and the material is allowed to dry. A coating can if required be applied (coated granules), which enables the active ingredient to be released in controlled amounts over a specific period of time.

FORMULATION EXAMPLES FOR LIQUID ACTIVE INGREDIENTS OF THE FORMULA I (%=PERCENT BY WEIGHT)

| 1. Emulsion concentrates | (a) | (b) | (c) |
|---|---|---|---|
| active ingredient from Table 1 | 25% | 40% | 50% |
| calcium dodecylbenzenesulfonate | 5% | 8% | 6% |
| castor oil-polyethylene glycol ether (36 mols of ethylene oxide) | 5% | — | — |
| tributylphenol-polyethylene glycol ether (30 mols of ethylene oxide) | — | 12% | 4% |
| cyclohexanone | — | 15% | 20% |
| xylene mixture | 65% | 25% | 20% |

Emulsions of the concentration required can be produced from concentrates of this type by dilution with water.

| 2. Solutions | (a) | (b) | (c) | (d) |
|---|---|---|---|---|
| active ingredient from Table 1 | 80% | 10% | 5% | 95% |
| ethylene glycol-monomethyl ether | 20% | — | — | — |
| polyethylene glycol M.W. 400 | — | 70% | — | — |
| N—methyl-2-pyrrolidone | — | 20% | — | — |
| epoxidised coconut oil | — | — | 1% | 5% |
| ligroin (boiling limits 160–190° C.) | — | — | 94% | — |

The solutions are suitable for application in the form of very fine drops.

| 3. Granulates | (a) | (b) |
|---|---|---|
| active ingredient from Table 1 | 5% | 10% |
| kaolin | 94% | — |
| highly dispersed silicic acid | 1% | — |
| attapulgite | — | 90% |

The active ingredient is dissolved in methylene chloride, the solution is sprayed onto the carrier, and the solvent is subsequently evaporated off in vacuo.

| 4. Dusts | (a) | (b) |
|---|---|---|
| active ingredient from Table 1 | 2% | 5% |
| highly dispersed silicic acid | 1% | 5% |
| talcum | 97% | — |
| kaolin | — | 90% |

Ready-for-use dusts are obtained by the intimate mixing together of the carriers with the active ingredient.

FORMULATION EXAMPLES FOR SOLID ACTIVE INGREDIENTS OF THE FORMULA I (%=PERCENT BY WEIGHT)

| 5. Wettable powders | (a) | (b) | (c) |
|---|---|---|---|
| active ingredient from Table 1 | 25% | 50% | 75% |
| sodium lignin sulfonate | 5% | 5% | — |
| sodium lauryl sulfate | 3% | — | 5% |
| sodium diisobutylnaphthalene sulfonate | — | 6% | 10% |
| octylphenolpolyethylene glycol ether (7–8 mols of ethylene oxide) | — | 2% | — |
| highly dispersed silicic acid | 5% | 10% | 10% |
| kaolin | 62% | 27% | — |

The active ingredient is well mixed with the additives and the mixture is thoroughly ground in a suitable mill. Wettable powders which can be diluted with water to give suspensions of the concentration required are obtained.

| 6. Emulsion concentrate | |
|---|---|
| active ingredient from Table 1 | 10% |
| octylphenolpolyethylene glycol ether | 3% |

| 6. Emulsion concentrate | |
|---|---|
| (4–5 mols of ethylene oxide) calcium dodecylbenzenesulfonate | 3% |
| castor oil polyglycol ether (35 mols of ethylene oxide) | 4% |
| cyclohexanone | 30% |
| xylene mixture | 50% |

Emulsions of any required concentration can be obtained from this concentrate by dilution with water.

| 7. Dusts | (a) | (b) |
|---|---|---|
| active ingredient from Table 1 | 5% | 8% |
| talcum | 95% | — |
| kaolin | — | 92% |

Dusts ready for use are obtained by mixing the active ingredient with the carriers and grinding the mixture in a suitable mill.

| 8. Extruder granulate | |
|---|---|
| active ingredient from Table 1 | 10% |
| sodium lignin sulfonate | 2% |
| carboxymethylcellulose | 1% |
| kaolin | 87% |

The active ingredient is mixed and ground with the additives, and the mixture is moistened with water. This mixture is extruded and subsequently dried in a stream of air.

| 9. Coated granulate | |
|---|---|
| active ingredient from Table 1 | 3% |
| polyethylene glycol (M.W. 200) | 3% |
| kaolin | 94% |

The finely ground active ingredient is evenly applied, in a mixer, to the kaolin moistened with polyethylene glycol. Dustfree coated granules are obtained in this manner.

| 10. Suspension concentrate | |
|---|---|
| active ingredient from Table 1 | 40% |
| ethylene glycol | 10% |
| nonylphenolpolyethylene glycol ether (15 mols of ethylene oxide) | 6% |
| sodium lignin sulfonate | 10% |
| carboxymethylcellulose | 1% |
| 37% aqueous formaldehyde solution | 0.2% |
| silicone oil in the form of a 75% aqueous emulsion | 0.8% |
| water | 32% |

The finely ground active ingredient is intimately mixed with the additives. There is thus obtained a suspension concentrate from which can be produced, by dilution with water, suspension of any concentration required.

FORMULATION EXAMPLES FOR ACTIVE-INGREDIENT MIXTURES (LIQUID) [%=PER CENT BY WEIGHT]

| 11. Emulsion concentrates | (a) | (b) | (c) |
|---|---|---|---|
| active-ingredient mixture: antidote from Table 1 and a herbicide of the formula II in the ratio of 1:1 | 25% | 40% | 50% |
| calcium dodecylbenzenesulfonate | 5% | 8% | 6% |
| castor oil-polyethylene glycol ether (36 mols of ethylene oxide) | 5% | — | — |
| tributylphenol-polyethylene glycol ether (30 mols of ethylene oxide) | — | 12% | 4% |
| cyclohexanone | — | 15% | 20% |
| xylene mixture | 65% | 25% | 20% |

Emulsions of the concentration required can be produced from concentrates of this type by dilution with water.

| 12. Emulsion concentrates | (a) | (b) | (c) |
|---|---|---|---|
| active-ingredient mixture: antidote from Table 1 and a herbicide of the formula II in the ratio of 1:3 | 25% | 40% | 50% |
| calcium dodecylbenzenesulfonate | 5% | 8% | 6% |
| castor oil-polyethylene glycol ether (36 mols of ethylene oxide) | 5% | — | — |
| tributylphenol-polyethylene glycol ether (30 mols of ethylene oxide) | — | 12% | 4% |
| cyclohexanone | — | 15% | 20% |
| xylene mixture | 65% | 25% | 20% |

Emulsions of any concentration required can be produced from concentrates of this type by dilution with water.

| 13. Emulsion concentrates | (a) | (b) | (c) |
|---|---|---|---|
| active-ingredient mixture: antidote from Table 1 and a herbicide of the formula II in the ratio of 2:1 | 25% | 40% | 50% |
| calcium dodecylbenzenesulfonate | 5% | 8% | 6% |
| castor oil-polyethylene glycol ether (36 mols of ethylene oxide) | 5% | — | — |
| tributylphenol-polyethylene glycol (30 mols of ethylene oxide) | — | 12% | 4% |
| cyclohexanone | — | 15% | 20% |
| xylene mixture | 65% | 25% | 20% |

Emulsions of any concentration required can be produced from concentrates of this type by dilution with water.

| 14. Emulsion concentrates | (a) | (b) | (c) |
|---|---|---|---|
| active-ingredient mixture: antidote from Table 1 and 2-[4-(5-chloro-3-fluoropyridin-2-yloxy)-phenoxy]-propionic acid methyl ester in the ratio of 1:1 | 25% | 40% | 50% |
| calcium dodecylbenzenesulfonate | 5% | 8% | 6% |
| castor oil-polyethylene glycol ether (36 mols of ethylene oxide) | 5% | — | — |
| tributylphenol-polyethylene glycol ether (30 mols of ethylene oxide) | — | 12% | 4% |
| cyclohexanone | — | 15% | 20% |
| xylene mixture | 65% | 25% | 20% |

Emulsions of any concentration required can be produced from concentrates of this type by dilution with water.

| 15. Emulsion concentrates | (a) | (b) | (c) |
|---|---|---|---|
| active-ingredient mixture: antidote from Table 1 and 2-[4-(5-chloro-3-fluoropyridin-2-yloxy)-phenoxy]-propionic acid methyl ester in the ratio of 1:3 | 25% | 40% | 50% |
| calcium dodecylbenzenesulfonate | 5% | 8% | 6% |
| castor oil-polyethylene glycol (36 mols of ethylene oxide) | 5% | — | — |
| tributylphenol-polyethylene glycol (30 mols of ethylene oxide) | — | 12% | 4% |
| cyclohexanone | — | 15% | 20% |
| xylene mixture | 65% | 25% | 20% |

Emulsions of any required concentration can be produced from concentrates of this type by dilution with water.

| 16. Solutions | (a) | (b) | (c) | (d) |
|---|---|---|---|---|
| active-ingredient mixture: antidote from Table 1 and a herbicide of the formula II in the ratio of 1:4 | 80% | 10% | 5% | 95% |
| ethylene glycol-monomethyl ether | 20% | — | — | — |
| polyethylene glycol (M.W. 400) | — | 70% | — | — |
| N—methyl-2-pyrrolidone | — | 20% | — | — |
| epoxidised coconut oil | — | — | 1% | 5% |
| ligroin (boiling limits 160–190° C.) | — | — | 94% | — |

The solutions are suitable for application in the form of very fine drops.

| 17. Solutions | (a) | (b) | (c) | (d) |
|---|---|---|---|---|
| active-ingredient mixture: antidote from Table 1 and a herbicide of the formula II in the ratio of 5:2 | 80% | 10% | 5% | 95% |
| ethylene glycol-monomethyl ether | 20% | — | — | — |
| polyethylene glycol (M.W. 400) | — | 70% | — | — |
| N—methyl-2-pyrrolidone | — | 20% | — | — |
| epoxidised coconut oil | — | — | 1% | 5% |
| ligroin (boiling limits 160–190° C.) | — | — | 94% | — |

The solutions are suitable for application in the form of very fine drops.

| 18. Solutions | (a) | (b) | (c) | (d) |
|---|---|---|---|---|
| active-ingredient mixture: antidote from Table 1 and a herbicide of the formula II in the ratio of 1:1 | 80% | 10% | 5% | 95% |
| ethylene glycol-monomethyl ether | 20% | — | — | — |
| polyethylene glycol (M.W. 400) | — | 70% | — | — |
| N—methyl-2-pyrrolidone | — | 20% | — | — |
| epoxidised coconut oil | — | — | 1% | 5% |
| ligroin (boiling limits 160–190° C.) | — | — | 94% | — |

The solutions are suitable for application in the form of very fine drops.

| 19. Solutions | (a) | (b) | (c) | (d) |
|---|---|---|---|---|
| active-ingredient mixture: antidote from Table 1 and 2-[4-(5-chloro-3-fluoropyridin-2-yloxy)-phenoxy]-propionic acid methyl ester in the ratio of 1:1 | 80% | 10% | 5% | 95% |
| ethylene glycol-monomethyl ether | 20% | — | — | — |
| polyethylene glycol (M.W. 400) | — | 70% | — | — |
| N—methyl-2-pyrrolidone | — | 20% | — | — |
| epoxidised coconut oil | — | — | 1% | 5% |
| ligroin (boiling limits 160–190° C.) | — | — | 94% | — |

The solutions are suitable for application in the form of very fine drops.

| 20. Solutions | (a) | (b) | (c) | (c) |
|---|---|---|---|---|
| active-ingredient mixture: antidote from Table 1 and 2-[4-(5-chloro-3-fluoropyridin-2-yloxy)-phenoxy]-propionic acid methyl ester in the ratio of 1:4 | 80% | 10% | 5% | 95% |
| ethylene glycol-monomethyl ether | 20% | — | — | — |
| polyethylene glycol (M.W. 400) | — | 70% | — | — |
| N—methyl-2-pyrrolidone | — | 20% | — | — |
| epoxidised coconut oil | — | — | 1% | 5% |
| ligroin (boiling limits 160–190° C.) | — | — | 94% | — |

The solutions are suitable for application in the form of very fine drops.

| 21. Granulates | (a) | (b) |
|---|---|---|
| active-ingredient mixture: antidote from Table 1 and a herbicide of the formula II in the ratio of 1:1 | 5% | 10% |
| kaolin | 94% | — |
| highly dispersed silicic acid | 1% | — |
| attapulgite | — | 90% |

The active ingredient is dissolved in methylene chloride, the solution is sprayed onto the carrier, and the solvent is subsequently evaporated off in vacuo.

| 22. Granulates | (a) | (b) |
|---|---|---|
| active-ingredient mixture: antidote from Table 1 and 2-[4-(5-chloro-3-fluoropyridin-2-yloxy)-phenoxy]-propionic acid methyl ester in the ratio of 1:1 | 5% | 10% |
| kaolin | 94% | — |
| highly dispersed silicic acid | 1% | — |
| attapulgite | — | 90% |

The active ingredient is dissolved in methylene chloride, the solution is sprayed onto the carrier, and the solvent is subsequently evaporated off in vacuo.

| 23. Dusts | (a) | (b) |
|---|---|---|
| active ingredient mixture: antidote from Table 1 and a herbicide of the formula II in the ratio of 1:1 | 2% | 5% |
| highly dispersed silicic acid | 1% | 5% |
| talcum | 97% | — |
| kaolin | — | 90% |

Ready-for-use dusts are obtained by the intimate mixing together of the carriers with the active ingredient.

FORMULATION EXAMPLES FOR
ACTIVE-INGREDIENT MIXTURES (SOLID)
(%=PERCENT BY WEIGHT)

| 24. Wettable powders | (a) | (b) | (c) |
|---|---|---|---|
| active-ingredient mixture: antidote from Table 1 and a herbicide of the formula II in the ratio of 1:1 | 25% | 50% | 75% |
| sodium lignin sulfonate | 5% | 5% | — |
| sodium lauryl sulfate | 3% | — | 5% |
| sodium diisobutylnaphthalene sulfonate | — | 6% | 10% |
| octylphenolpolyethylene glycol ether (7–8 mols of ethylene oxide) | — | 2% | — |
| highly dispersed silicic acid | 5% | 10% | 10% |

| 24. Wettable powders | (a) | (b) | (c) |
|---|---|---|---|
| kaolin | 62% | 27% | — |

The active ingredient is well mixed with the additives and the mixture is thoroughly ground in a suitable mill. Wettable powders which can be diluted with water to give suspensions of any required concentration are obtained.

| 25. Wettable powders | (a) | (b) | (c) |
|---|---|---|---|
| active-ingredient mixture: antidote from Table 1 and a herbicide of the formula II in the ratio of 1:4 | 25% | 50% | 75% |
| sodium lignin sulfonate | 5% | 5% | — |
| sodium lauryl sulfate | 3% | — | 5% |
| sodium diisobutylnaphthalene sulfonate | — | 6% | 10% |
| octylphenolpolyethylene glycol ether (7–8 mols of ethylene oxide) | — | 2% | — |
| highly dispersed silicic acid | 5% | 10% | 10% |
| kaolin | 62% | 27% | — |

The active ingredient is well mixed with the additives and the mixture thoroughly ground in a suitable mill. Wettable powders which can be diluted with water to give suspensions of any required concentration are obtained.

| 26. Wettable powders | (a) | (b) | (c) |
|---|---|---|---|
| active-ingredient mixture: antidote from Table 1 and a herbicide of the formula II in the ratio of 3:1 | 25% | 50% | 75% |
| sodium lignin sulfonate | 5% | 5% | — |
| sodium lauryl sulfate | 3% | — | 5% |
| sodium diisobutylnaphthalene sulfonate | — | 6% | 10% |
| octylphenolpolyethylene glycol ether (7–8 mols of ethylene oxide) | — | 2% | — |
| highly dispersed silicic acid | 5% | 10% | 10% |
| kaolin | 62% | 27% | — |

The active ingredient is well mixed with the additives and the mixture is thoroughly ground in a suitable mill. Wettable powders which can be diluted with water to give suspensions of the concentration required are obtained.

| 27. Emulsion concentrate | |
|---|---|
| active-ingredient mixture: antidote from Table 1 and a herbicide of the formula II in the ratio of 1:1 | 10% |
| octylphenolpolyethylene glycol ether (4–5 mols of ethylene oxide) | 3% |
| calcium dodecylbenzenesulfonate | 3% |
| castor-oil-polyglycol ether (35 mols of ethylene oxide) | 4% |
| cyclohexanone | 30% |
| xylene mixture | 50% |

Emulsions of any required concentration are obtained from this concentrate by dilution with water.

| 28. Emulsion concentrate | |
|---|---|
| active-ingredient mixture: antidote from Table 1 and a herbicide of the formula II in the ratio of 5:2 | 10% |
| octylphenolpolyethylene glycol ether (4–5 mols of ethylene oxide) | 3% |
| calcium dodecylbenzenesulfonate | 3% |
| castor oil-polyglycol ether (35 mols of ethylene oxide) | 4% |
| cyclohexanone | 30% |
| xylene mixture | 50% |

Emulsions of any required concentration are obtained from this concentrate by dilution with water.

| 29. Emulsion concentrate | |
|---|---|
| active-ingredient mixture: antidote from Table 1 and a herbicide of the formula II in the ratio of 1:4 | 10% |
| octylphenolpolyethylene glycol ether (4–5 mols of ethylene oxide) | 3% |
| calcium dodecylbenzene sulfonate | 3% |
| castor oil-polyglycol ether (35 mols of ethylene oxide) | 4% |
| cyclohexanone | 30% |
| xylene mixture | 50% |

Emulsions of any required concentration are produced from this concentrate by dilution with water.

| 30. Dusts | (a) | (b) |
|---|---|---|
| active-ingredient mixture: antidote from Table 1 and a herbicide of the formula II in the ratio of 1:1 | 5% | 8% |
| talcum | 95% | — |
| kaolin | — | 92% |

Dusts ready for use are obtained by mixing the active ingredient with the carriers and grinding the mixture in a suitable mill.

| 31. Extruder granulate | |
|---|---|
| active ingredient mixture: antidote from Table 1 and a herbicide of the formula II in the ratio of 1:1 | 10% |
| sodium lignin sulfonate | 2% |
| carboxymethylcellulose | 1% |
| kaolin | 87% |

The active ingredient is mixed and ground with the additives, and the mixture is moisted with water. This mixture is extruded and subsequently dried in a stream of air.

| 32. Coated granulate | |
|---|---|
| active-ingredient mixture: antidote from Table 1 and a herbicide of the formula II in the ratio of 1:1 | 3% |
| polyethylene glycol (M.W. 200) | 3% |
| kaolin | 94% |

The finely ground active ingredient is evenly applied in a mixer to the kaolin moistened with polyethylene glycol. Dustfree coated granules are obtained in this manner.

| 33. Suspension concentrate | |
|---|---|
| active ingredient mixture: antidote from Table 1 and a herbicide of the formula II in the ratio of 1:1 | 40% |
| ethylene glycol | 10% |

-continued

33. Suspension concentrate

| | |
|---|---|
| nonylphenolpolyethylene glycol ether (15 mols of ethylene oxide) | 6% |
| sodium lignin sulfonate | 10% |
| carboxymethylcellulose | 1% |
| 37% aqueous formaldehyde solution | 0.2% |
| silicone oil in the form of a 75% aqueous emulsion | 0.8% |
| water | 32% |

The finely ground active ingredient is intimately mixed with the additives. There is thus obtained a suspension concentrate from which can be produced, by dilution with water, suspensions of the concentration required.

34. Suspension concentrate

| | |
|---|---|
| active-ingredient mixture: antidote from Table 1 and a herbicide of the formula II in the ratio of 1:4 | 40% |
| ethylene glycol | 10% |
| nonylphenolpolyethylene glycol ether (15 mols of ethylene oxide) | 6% |
| sodium lignin sulfonate | 10% |
| carboxymethylcellulos | 1% |
| 37% aqueous formaldehyde solution | 0.2% |
| silicone oil in the form of a 75% aqueous emulsion | 0.8% |
| water | 32% |

The finely ground active ingredient is intimately mixed with the additives. There is obtained a suspension concentrate from which can be produced, by dilution with water, suspensions of any concentration required.

35. Suspension concentrate

| | |
|---|---|
| active-ingredient mixture: antidote from Table 1 and a herbicide of the formula II in the ratio of 3:1 | 40% |
| ethylene glycol | 10% |
| nonylphenolpolyethylene glycol ether (15 mols of ethylene oxide) | 6% |
| sodium lignin sulfonate | 10% |
| carboxymethylcellulose | 1% |
| 37% aqueous formaldehyde solution | 0.2% |
| silicone oil in the form of a 75% aqueous emulsion | 0.8% |
| water | 32% |

The finely ground active ingredient is intimately mixed with the additives. There is thus obtained a suspension concentrate from which can be produced, by dilution with water, suspensions of the concentration required.

BIOLOGICAL EXAMPLES

Test description

Seeds of the plants to be tested are sown in plastic pots each containing 0.5 liter of soil in a greenhouse. When the plants have reached the 2- to 3-leaf stage, a safener (antidote) of the formula I and a herbicide of the formula II are applied together as a tank mixture. The protective action of the safener is assessed in percent 21 days after application. Reference values are provided by plants treated with the herbicide alone and by completely untreated control plants. The results are summarised in the following Table 3.

TABLE 3

Relative protective action in per cent in spring wheat, variety "Besso", and in spring barley, variety "Cornel".

| Safener Comp. No. | Applied amount g of a.i.* per ha | Herbi-cide No. | Applied amount g of a.i. per ha | Relative protective action in wheat in % | Relative protective action in barley in % |
|---|---|---|---|---|---|
| 1.125 | 31 | 2.1 | 125 | 10 | 30 |
| 1.125 | 62 | 2.1 | 125 | 0 | 25 |
| 1.125 | 125 | 2.1 | 125 | 10 | 30 |
| 1.125 | 62 | 2.1 | 250 | 70 | 15 |
| 1.125 | 125 | 2.1 | 250 | 65 | 25 |
| 1.125 | 250 | 2.1 | 250 | 65 | 15 |
| 1.125 | 125 | 2.1 | 500 | 80 | 13 |
| 1.125 | 250 | 2.1 | 500 | 75 | 8 |
| 1.125 | 500 | 2.1 | 500 | 75 | 18 |
| 1.125 | 31 | 2.6 | 125 | 20 | 60 |
| 1.125 | 62 | 2.6 | 125 | 20 | 70 |
| 1.125 | 125 | 2.6 | 125 | 20 | 65 |
| 1.125 | 62 | 2.6 | 250 | 50 | 45 |
| 1.125 | 125 | 2.6 | 250 | 55 | 50 |
| 1.125 | 250 | 2.6 | 250 | 50 | 45 |
| 1.125 | 125 | 2.6 | 500 | 70 | 35 |
| 1.125 | 250 | 2.6 | 500 | 70 | 45 |
| 1.125 | 500 | 2.6 | 500 | 65 | 35 |
| 1.125 | 31 | 2.8 | 125 | 0 | 35 |
| 1.125 | 62 | 2.8 | 125 | 0 | 35 |
| 1.125 | 125 | 2.8 | 125 | 0 | 30 |
| 1.125 | 62 | 2.8 | 250 | 10 | 45 |
| 1.125 | 125 | 2.8 | 250 | 5 | 45 |
| 1.125 | 250 | 2.8 | 250 | 10 | 30 |
| 1.125 | 125 | 2.8 | 500 | 40 | 40 |
| 1.125 | 250 | 2.8 | 500 | 40 | 40 |
| 1.125 | 500 | 2.8 | 500 | 35 | 35 |
| 1.125 | 31 | 2.9 | 125 | 10 | 65 |
| 1.125 | 62 | 2.9 | 125 | 15 | 60 |
| 1.125 | 125 | 2.9 | 125 | 15 | 75 |
| 1.125 | 62 | 2.9 | 250 | 50 | 60 |
| 1.125 | 125 | 2.9 | 250 | 45 | 55 |
| 1.125 | 250 | 2.9 | 250 | 30 | 60 |
| 1.125 | 125 | 2.9 | 500 | 75 | 50 |
| 1.125 | 250 | 2.9 | 500 | 65 | 45 |
| 1.125 | 500 | 2.9 | 500 | 65 | 45 |
| 1.130 | 31 | 2.1 | 125 | 5 | 5 |
| 1.130 | 62 | 2.1 | 125 | 10 | 5 |
| 1.130 | 125 | 2.1 | 125 | 0 | 5 |
| 1.130 | 62 | 2.1 | 250 | 70 | 0 |
| 1.130 | 125 | 2.1 | 250 | 60 | 0 |
| 1.130 | 250 | 2.1 | 250 | 70 | 0 |
| 1.130 | 125 | 2.1 | 500 | 70 | 8 |
| 1.130 | 250 | 2.1 | 500 | 75 | 8 |
| 1.130 | 500 | 2.1 | 500 | 80 | 8 |
| 1.130 | 31 | 2.6 | 125 | 15 | 5 |
| 1.130 | 62 | 2.6 | 125 | 20 | 5 |
| 1.130 | 125 | 2.6 | 125 | 20 | 5 |
| 1.130 | 62 | 2.6 | 250 | 65 | 0 |
| 1.130 | 125 | 2.6 | 250 | 65 | 0 |
| 1.130 | 250 | 2.6 | 250 | 65 | 0 |
| 1.130 | 125 | 2.6 | 500 | 65 | 0 |
| 1.130 | 250 | 2.6 | 500 | 75 | 0 |
| 1.130 | 500 | 2.6 | 500 | 80 | 0 |
| 1.130 | 31 | 2.8 | 125 | 0 | 15 |
| 1.130 | 62 | 2.8 | 125 | 0 | 0 |
| 1.130 | 125 | 2.8 | 125 | 0 | 0 |
| 1.130 | 62 | 2.8 | 250 | 15 | 5 |
| 1.130 | 125 | 2.8 | 250 | 15 | 0 |
| 1.130 | 250 | 2.8 | 250 | 5 | 5 |
| 1.130 | 125 | 2.8 | 500 | 40 | 0 |
| 1.130 | 250 | 2.8 | 500 | 40 | 0 |
| 1.130 | 500 | 2.8 | 500 | 40 | 0 |
| 1.130 | 31 | 2.9 | 125 | 15 | 35 |
| 1.130 | 62 | 2.9 | 125 | 15 | 35 |
| 1.130 | 125 | 2.9 | 125 | 15 | 40 |
| 1.130 | 62 | 2.9 | 250 | 50 | 5 |
| 1.130 | 125 | 2.9 | 250 | 50 | 10 |
| 1.130 | 250 | 2.9 | 250 | 45 | 10 |
| 1.130 | 125 | 2.9 | 500 | 55 | 5 |
| 1.130 | 250 | 2.9 | 500 | 60 | 5 |
| 1.130 | 500 | 2.9 | 500 | 70 | 5 |
| 1.134 | 31 | 2.1 | 125 | 10 | 35 |
| 1.134 | 62 | 2.1 | 125 | 10 | 45 |
| 1.134 | 125 | 2.1 | 125 | 5 | 45 |

TABLE 3-continued

Relative protective action in per cent in spring wheat, variety "Besso", and in spring barley, variety "Cornel".

| Safener Comp. No. | Applied amount g of a.i.* per ha | Herbicide No. | Applied amount g of a.i. per ha | Relative protective action in wheat in % | Relative protective action in barley in % |
|---|---|---|---|---|---|
| 1.134 | 62 | 2.1 | 250 | 75 | 20 |
| 1.134 | 125 | 2.1 | 250 | 70 | 15 |
| 1.134 | 250 | 2.1 | 250 | 65 | 15 |
| 1.134 | 125 | 2.1 | 500 | 80 | 8 |
| 1.134 | 250 | 2.1 | 500 | 75 | 8 |
| 1.134 | 500 | 2.1 | 500 | 70 | 13 |
| 1.134 | 31 | 2.6 | 125 | 20 | 45 |
| 1.134 | 62 | 2.6 | 125 | 15 | 55 |
| 1.134 | 125 | 2.6 | 125 | 20 | 65 |
| 1.134 | 62 | 2.6 | 250 | 60 | 45 |
| 1.134 | 125 | 2.6 | 250 | 60 | 50 |
| 1.134 | 250 | 2.6 | 250 | 65 | 50 |
| 1.134 | 125 | 2.6 | 500 | 90 | 20 |
| 1.134 | 250 | 2.6 | 500 | 90 | 20 |
| 1.134 | 500 | 2.6 | 500 | 80 | 15 |
| 1.134 | 31 | 2.8 | 125 | 5 | 45 |
| 1.134 | 62 | 2.8 | 125 | 0 | 45 |
| 1.134 | 125 | 2.8 | 125 | 0 | 40 |
| 1.134 | 62 | 2.8 | 250 | 10 | 50 |
| 1.134 | 125 | 2.8 | 250 | 10 | 45 |
| 1.134 | 250 | 2.8 | 250 | 10 | 40 |
| 1.134 | 125 | 2.8 | 500 | 40 | 30 |
| 1.134 | 250 | 2.8 | 500 | 35 | 30 |
| 1.134 | 500 | 2.8 | 500 | 35 | 30 |
| 1.134 | 31 | 2.9 | 125 | 20 | 65 |
| 1.134 | 62 | 2.9 | 125 | 20 | 65 |
| 1.134 | 125 | 2.9 | 125 | 20 | 60 |
| 1.134 | 62 | 2.9 | 250 | 45 | 45 |
| 1.134 | 125 | 2.9 | 250 | 50 | 60 |
| 1.134 | 250 | 2.9 | 250 | 45 | 55 |
| 1.134 | 125 | 2.9 | 500 | 70 | 40 |
| 1.134 | 250 | 2.9 | 500 | 70 | 40 |
| 1.134 | 500 | 2.9 | 500 | 70 | 55 |
| 1.186 | 31 | 2.1 | 125 | 10 | 45 |
| 1.186 | 62 | 2.1 | 125 | 15 | 35 |
| 1.186 | 125 | 2.1 | 125 | 15 | 45 |
| 1.186 | 62 | 2.1 | 250 | 75 | 15 |
| 1.186 | 125 | 2.1 | 250 | 65 | 20 |
| 1.186 | 250 | 2.1 | 250 | 70 | 15 |
| 1.186 | 125 | 2.1 | 500 | 85 | 13 |
| 1.186 | 250 | 2.1 | 500 | 85 | 13 |
| 1.186 | 500 | 2.1 | 500 | 75 | 13 |
| 1.186 | 31 | 2.6 | 125 | 20 | 50 |
| 1.186 | 62 | 2.6 | 125 | 20 | 60 |
| 1.186 | 125 | 2.6 | 125 | 20 | 60 |
| 1.186 | 62 | 2.6 | 250 | 50 | 35 |
| 1.186 | 125 | 2.6 | 250 | 55 | 45 |
| 1.186 | 250 | 2.6 | 250 | 55 | 50 |
| 1.186 | 125 | 2.6 | 500 | 90 | 25 |
| 1.186 | 250 | 2.6 | 500 | 85 | 20 |
| 1.186 | 500 | 2.6 | 500 | 70 | 20 |
| 1.186 | 31 | 2.8 | 125 | 0 | 35 |
| 1.186 | 62 | 2.8 | 125 | 0 | 45 |
| 1.186 | 125 | 2.8 | 125 | 0 | 35 |
| 1.186 | 62 | 2.8 | 250 | 0 | 35 |
| 1.186 | 125 | 2.8 | 250 | 0 | 45 |
| 1.186 | 250 | 2.8 | 250 | 0 | 40 |
| 1.186 | 125 | 2.8 | 500 | 35 | 25 |
| 1.186 | 250 | 2.8 | 500 | 35 | 25 |
| 1.186 | 500 | 2.8 | 500 | 25 | 25 |
| 1.186 | 31 | 2.9 | 125 | 20 | 40 |
| 1.186 | 62 | 2.9 | 125 | 20 | 65 |
| 1.186 | 125 | 2.9 | 125 | 20 | 60 |
| 1.186 | 62 | 2.9 | 250 | 50 | 35 |
| 1.186 | 125 | 2.9 | 250 | 40 | 45 |
| 1.186 | 250 | 2.9 | 250 | 50 | 55 |
| 1.186 | 125 | 2.9 | 500 | 70 | 40 |
| 1.186 | 250 | 2.9 | 500 | 60 | 45 |
| 1.186 | 500 | 2.9 | 500 | 55 | 50 |
| 1.188 | 31 | 2.1 | 125 | 15 | 15 |
| 1.188 | 62 | 2.1 | 125 | 15 | 25 |
| 1.188 | 125 | 2.1 | 125 | 15 | 30 |
| 1.188 | 62 | 2.1 | 250 | 70 | 15 |
| 1.188 | 125 | 2.1 | 250 | 70 | 15 |
| 1.188 | 250 | 2.1 | 250 | 60 | 15 |
| 1.188 | 125 | 2.1 | 500 | 90 | 13 |
| 1.188 | 250 | 2.1 | 500 | 85 | 8 |
| 1.188 | 500 | 2.1 | 500 | 80 | 8 |
| 1.188 | 31 | 2.6 | 125 | 20 | 55 |
| 1.188 | 62 | 2.6 | 125 | 20 | 50 |
| 1.188 | 125 | 2.6 | 125 | 20 | 55 |
| 1.188 | 62 | 2.6 | 250 | 65 | 30 |
| 1.188 | 125 | 2.6 | 250 | 65 | 50 |
| 1.188 | 250 | 2.6 | 250 | 60 | 50 |
| 1.188 | 125 | 2.6 | 500 | 85 | 20 |
| 1.188 | 250 | 2.6 | 500 | 85 | 30 |
| 1.188 | 500 | 2.6 | 500 | 80 | 30 |
| 1.188 | 31 | 2.8 | 125 | 5 | 50 |
| 1.188 | 62 | 2.8 | 125 | 5 | 55 |
| 1.188 | 125 | 2.8 | 125 | 0 | 50 |
| 1.188 | 62 | 2.8 | 250 | 10 | 65 |
| 1.188 | 125 | 2.8 | 250 | 10 | 60 |
| 1.188 | 250 | 2.8 | 250 | 10 | 60 |
| 1.188 | 125 | 2.8 | 500 | 30 | 35 |
| 1.188 | 250 | 2.8 | 500 | 30 | 35 |
| 1.188 | 500 | 2.8 | 500 | 35 | 30 |
| 1.188 | 31 | 2.9 | 125 | 20 | 50 |
| 1.188 | 62 | 2.9 | 125 | 20 | 55 |
| 1.188 | 125 | 2.9 | 125 | 20 | 50 |
| 1.188 | 62 | 2.9 | 250 | 50 | 50 |
| 1.188 | 125 | 2.9 | 250 | 50 | 45 |
| 1.188 | 250 | 2.9 | 250 | 45 | 40 |
| 1.188 | 125 | 2.9 | 500 | 75 | 30 |
| 1.188 | 250 | 2.9 | 500 | 70 | 40 |
| 1.188 | 500 | 2.9 | 500 | 75 | 40 |
| 1.245 | 250 | 2.1 | 500 | 70 | — |
| 1.245 | 500 | 2.1 | 500 | 65 | — |
| 1.245 | 250 | 2.1 | 1000 | 50 | — |
| 1.245 | 500 | 2.1 | 1000 | 45 | — |
| 1.245 | 62 | 2.8 | 250 | 55 | 50 |
| 1.245 | 125 | 2.8 | 250 | 65 | 55 |
| 1.245 | 125 | 2.8 | 500 | 75 | 58 |
| 1.245 | 250 | 2.8 | 500 | 90 | 48 |
| 1.247 | 250 | 2.1 | 500 | 65 | — |
| 1.247 | 500 | 2.1 | 500 | 75 | — |
| 1.247 | 250 | 2.1 | 1000 | 45 | — |
| 1.247 | 500 | 2.1 | 1000 | 65 | — |
| 1.247 | 62 | 2.8 | 250 | 70 | — |
| 1.247 | 125 | 2.8 | 250 | 70 | — |
| 1.247 | 125 | 2.8 | 500 | 80 | — |
| 1.247 | 250 | 2.8 | 500 | 80 | — |
| 1.248 | 250 | 2.1 | 500 | 65 | — |
| 1.248 | 500 | 2.1 | 500 | 65 | — |
| 1.248 | 250 | 2.1 | 1000 | 40 | — |
| 1.248 | 500 | 2.1 | 1000 | 50 | — |
| 1.248 | 62 | 2.8 | 250 | 70 | 60 |
| 1.248 | 125 | 2.8 | 250 | 70 | 75 |
| 1.248 | 125 | 2.8 | 500 | 90 | 68 |
| 1.248 | 250 | 2.8 | 500 | 90 | 73 |
| 1.255 | 62 | 2.8 | 250 | — | 70 |
| 1.255 | 125 | 2.8 | 250 | — | 70 |
| 1.255 | 125 | 2.8 | 500 | — | 70 |
| 1.255 | 250 | 2.8 | 500 | — | 50 |
| 1.256 | 250 | 2.1 | 500 | 65 | — |
| 1.256 | 500 | 2.1 | 500 | 65 | — |
| 1.256 | 250 | 2.1 | 1000 | 60 | — |
| 1.256 | 500 | 2.1 | 1000 | 50 | — |
| 1.256 | 62 | 2.8 | 250 | 60 | 65 |
| 1.256 | 125 | 2.8 | 250 | 65 | 60 |
| 1.256 | 125 | 2.8 | 500 | 85 | 43 |
| 1.256 | 250 | 2.8 | 500 | 80 | 73 |
| 1.259 | 62 | 2.8 | 250 | — | 60 |
| 1.259 | 125 | 2.8 | 250 | — | 75 |
| 1.259 | 125 | 2.8 | 500 | — | 53 |
| 1.259 | 250 | 2.8 | 500 | — | 68 |
| 1.260 | 62 | 2.8 | 250 | — | 65 |
| 1.260 | 125 | 2.8 | 250 | — | 60 |
| 1.260 | 125 | 2.8 | 250 | — | 53 |
| 1.260 | 125 | 2.8 | 500 | — | 58 |
| 1.260 | 250 | 2.8 | 500 | — | 53 |

TABLE 3-continued

Relative protective action in per cent in spring wheat, variety "Besso", and in spring barley, variety "Cornel".

| Safener Comp. No. | Applied amount g of a.i.* per ha | Herbicide No. | Applied amount g of a.i. per ha | Relative protective action in wheat in % | Relative protective action in barley in % |
|---|---|---|---|---|---|
| 1.261 | 62 | 2.8 | 250 | — | 65 |
| 1.261 | 125 | 2.8 | 250 | — | 70 |
| 1.261 | 125 | 2.8 | 500 | — | 58 |
| 1.261 | 250 | 2.8 | 500 | — | 68 |
| 1.262 | 62 | 2.8 | 250 | — | 75 |
| 1.262 | 125 | 2.8 | 250 | — | 85 |
| 1.262 | 125 | 2.8 | 500 | — | 63 |
| 1.262 | 250 | 2.8 | 500 | — | 78 |
| 1.267 | 250 | 2.1 | 500 | 65 | — |
| 1.267 | 500 | 2.1 | 500 | 65 | — |
| 1.267 | 250 | 2.1 | 1000 | 55 | — |
| 1.267 | 250 | 2.1 | 1000 | 50 | — |
| 1.267 | 62 | 2.8 | 250 | 65 | 65 |
| 1.267 | 125 | 2.8 | 250 | 65 | 70 |
| 1.267 | 125 | 2.8 | 500 | 85 | 48 |
| 1.267 | 250 | 2.8 | 500 | 85 | 73 |
| 1.276 | 250 | 2.1 | 500 | 60 | — |
| 1.276 | 500 | 2.1 | 500 | 55 | — |
| 1.276 | 250 | 2.1 | 1000 | 35 | — |
| 1.276 | 500 | 2.1 | 1000 | 50 | — |
| 1.276 | 62 | 2.8 | 250 | 70 | 65 |
| 1.276 | 125 | 2.8 | 250 | 65 | 75 |
| 1.276 | 125 | 2.8 | 500 | 85 | 63 |
| 1.276 | 250 | 2.8 | 500 | 80 | 68 |
| 1.284 | 250 | 2.1 | 500 | 60 | — |
| 1.284 | 500 | 2.1 | 500 | 65 | — |
| 1.284 | 250 | 2.1 | 1000 | 50 | — |
| 1.284 | 500 | 2.1 | 1000 | 45 | — |
| 1.284 | 62 | 2.8 | 250 | 70 | 60 |
| 1.284 | 125 | 2.8 | 250 | 65 | 55 |
| 1.284 | 125 | 2.8 | 500 | 75 | 63 |
| 1.284 | 250 | 2.8 | 500 | 70 | 73 |
| 1.285 | 250 | 2.1 | 500 | 55 | — |
| 1.285 | 500 | 2.1 | 500 | 65 | — |
| 1.285 | 250 | 2.1 | 1000 | 40 | — |
| 1.285 | 500 | 2.1 | 1000 | 50 | — |
| 1.285 | 62 | 2.8 | 250 | 65 | 65 |
| 1.285 | 125 | 2.8 | 250 | 65 | 65 |
| 1.285 | 125 | 2.8 | 500 | 80 | 68 |
| 1.285 | 250 | 2.8 | 500 | 85 | 78 |
| 1.285 | 250 | 2.1 | 500 | 85 | 78 |
| 1.290 | 250 | 2.1 | 500 | 60 | — |
| 1.290 | 500 | 2.1 | 500 | 60 | — |
| 1.290 | 250 | 2.1 | 1000 | 45 | — |
| 1.290 | 500 | 2.1 | 1000 | 60 | — |
| 1.290 | 62 | 2.8 | 250 | 50 | 70 |
| 1.290 | 125 | 2.8 | 250 | 65 | 75 |
| 1.290 | 125 | 2.8 | 500 | 80 | 63 |
| 1.290 | 250 | 2.8 | 500 | 85 | 73 |
| 1.293 | 250 | 2.1 | 500 | 60 | — |
| 1.293 | 500 | 2.1 | 500 | 45 | — |
| 1.293 | 250 | 2.1 | 1000 | 45 | — |
| 1.293 | 500 | 2.1 | 1000 | 70 | — |
| 1.293 | 62 | 2.8 | 250 | 50 | 60 |
| 1.293 | 125 | 2.8 | 250 | 55 | 65 |
| 1.293 | 125 | 2.8 | 500 | 55 | 48 |
| 1.293 | 250 | 2.8 | 500 | 80 | 53 |
| 1.301 | 250 | 2.1 | 500 | 70 | — |
| 1.301 | 500 | 2.1 | 500 | 75 | — |
| 1.301 | 250 | 2.1 | 1000 | 50 | — |
| 1.301 | 500 | 2.1 | 1000 | 45 | — |
| 1.301 | 62 | 2.8 | 250 | 60 | — |
| 1.301 | 125 | 2.8 | 250 | 65 | — |
| 1.301 | 125 | 2.8 | 500 | 70 | — |
| 1.301 | 250 | 2.8 | 500 | 75 | — |
| 1.305 | 62 | 2.8 | 250 | — | 65 |
| 1.305 | 125 | 2.8 | 250 | — | 70 |
| 1.305 | 125 | 2.8 | 500 | — | 68 |
| 1.305 | 250 | 2.8 | 500 | — | 73 |
| 1.308 | 62 | 2.8 | 250 | — | 90 |
| 1.308 | 125 | 2.8 | 250 | — | 90 |
| 1.308 | 125 | 2.8 | 500 | — | 63 |
| 1.308 | 250 | 2.8 | 500 | — | 73 |
| 1.314 | 62 | 2.8 | 250 | — | 80 |
| 1.314 | 125 | 2.8 | 250 | — | 90 |
| 1.314 | 125 | 2.8 | 500 | — | 58 |
| 1.314 | 250 | 2.8 | 500 | — | 63 |
| 1.316 | 250 | 2.1 | 500 | 65 | — |
| 1.316 | 500 | 2.1 | 500 | 65 | — |
| 1.316 | 250 | 2.1 | 1000 | 35 | — |
| 1.316 | 500 | 2.1 | 1000 | 50 | — |
| 1.316 | 62 | 2.8 | 250 | — | 50 |
| 1.316 | 125 | 2.8 | 250 | — | 50 |
| 1.316 | 125 | 2.8 | 500 | — | 55 |
| 1.316 | 250 | 2.8 | 500 | — | 60 |
| 1.321 | 62 | 2.8 | 250 | — | 65 |
| 1.321 | 125 | 2.8 | 250 | — | 80 |
| 1.321 | 125 | 2.8 | 500 | — | 60 |
| 1.321 | 250 | 2.8 | 500 | — | 70 |
| 1.325 | 250 | 2.1 | 500 | 60 | — |
| 1.325 | 500 | 2.1 | 500 | 50 | — |
| 1.325 | 250 | 2.1 | 1000 | 50 | — |
| 1.325 | 500 | 2.1 | 1000 | 70 | — |
| 1.327 | 62 | 2.8 | 250 | — | 70 |
| 1.327 | 125 | 2.8 | 250 | — | 80 |
| 1.327 | 125 | 2.8 | 500 | — | 50 |
| 1.327 | 250 | 2.8 | 500 | — | 50 |
| 1.333 | 250 | 2.1 | 500 | 63 | — |
| 1.333 | 500 | 2.1 | 500 | 73 | — |
| 1.333 | 250 | 2.1 | 1000 | 35 | — |
| 1.333 | 500 | 2.1 | 1000 | 55 | — |
| 1.334 | 62 | 2.8 | 250 | — | 75 |
| 1.334 | 125 | 2.8 | 250 | — | 85 |
| 1.334 | 125 | 2.8 | 500 | — | 63 |
| 1.334 | 250 | 2.8 | 500 | — | 63 |
| 1.336 | 250 | 2.1 | 500 | 70 | — |
| 1.336 | 500 | 2.1 | 500 | 75 | — |
| 1.336 | 250 | 2.1 | 1000 | 45 | — |
| 1.336 | 500 | 2.1 | 1000 | 45 | — |
| 1.336 | 62 | 2.8 | 250 | 65 | 60 |
| 1.336 | 125 | 2.8 | 250 | 65 | 60 |
| 1.336 | 125 | 2.8 | 500 | 85 | 53 |
| 1.336 | 250 | 2.8 | 500 | 85 | 23 |
| 1.337 | 250 | 2.1 | 500 | 60 | — |
| 1.337 | 500 | 2.1 | 500 | 55 | — |
| 1.337 | 250 | 2.1 | 1000 | 45 | — |
| 1.337 | 500 | 2.1 | 1000 | 50 | — |
| 1.337 | 62 | 2.8 | 250 | 65 | 65 |
| 1.337 | 125 | 2.8 | 250 | 55 | 50 |
| 1.337 | 125 | 2.8 | 500 | 70 | 63 |
| 1.337 | 250 | 2.8 | 500 | 60 | 78 |
| 1.341 | 250 | 2.1 | 500 | 58 | — |
| 1.341 | 500 | 2.1 | 500 | 73 | — |
| 1.341 | 250 | 2.1 | 1000 | 25 | — |
| 1.341 | 500 | 2.1 | 1000 | 60 | — |
| 1.341 | 62 | 2.8 | 250 | — | 90 |
| 1.341 | 125 | 2.8 | 250 | — | 90 |
| 1.341 | 125 | 2.8 | 500 | — | 63 |
| 1.341 | 250 | 2.8 | 500 | — | 68 |
| 1.353 | 62 | 2.8 | 250 | — | 65 |
| 1.353 | 125 | 2.8 | 250 | — | 75 |
| 1.353 | 125 | 2.8 | 500 | — | 65 |
| 1.353 | 250 | 2.8 | 500 | — | 60 |
| 1.355 | 250 | 2.1 | 500 | 78 | — |
| 1.355 | 500 | 2.1 | 500 | 78 | — |
| 1.355 | 250 | 2.1 | 1000 | 45 | — |
| 1.355 | 500 | 2.1 | 1000 | 55 | — |
| 1.355 | 62 | 2.8 | 250 | 50 | — |
| 1.355 | 125 | 2.8 | 250 | 55 | — |
| 1.355 | 125 | 2.8 | 500 | 45 | — |
| 1.355 | 250 | 2.8 | 500 | 55 | — |
| 1.362 | 62 | 2.8 | 250 | — | 90 |
| 1.362 | 125 | 2.8 | 250 | — | 90 |
| 1.362 | 125 | 2.8 | 500 | — | 63 |
| 1.362 | 250 | 2.8 | 500 | — | 73 |
| 1.363 | 62 | 2.8 | 250 | — | 80 |
| 1.363 | 125 | 2.8 | 250 | — | 80 |
| 1.363 | 125 | 2.8 | 500 | — | 63 |

TABLE 3-continued

Relative protective action in per cent in spring wheat, variety "Besso", and in spring barley, variety "Cornel".

| Safener Comp. No. | Applied amount g of a.i.* per ha | Herbicide No. | Applied amount g of a.i. per ha | Relative protective action in wheat in % | Relative protective action in barley in % |
|---|---|---|---|---|---|
| 1.363 | 250 | 2.8 | 500 | — | 63 |

*a.i. = active ingredient
—: not tested

What is claimed is:

1. A process for selectively controlling *Avena ludoviciana*, and *Lolium perenne* in cereal crops, which process comprises treating the cereal crops, parts of the cereal crops or cultivated by for the cereal crops with an effective amount of an antidote of formula I

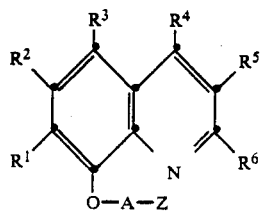

wherein $R^1$, $R^2$, $R^4$, $R^5$ and $R^6$ are hydrogen,
$R^3$ is hydrogen or chlorine,
A is $-CH_2-$,
Z is $COOR^{12}$ and
$R^{12}$ is an alkyl group of 4 to 11 carbon atoms and an effective amount of a herbicide of formula II

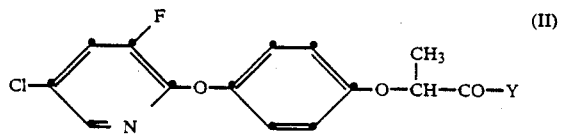

wherein
Y is $-OR^{18}$ and
$R^{18}$ is $C_3-C_9$ alkynyl.

2. A process of claim 1 in which process 2-[4-(5-chloro-3-fluoro-pyridin-2-yloxy)-phenoxy]-propionic acid propargylester is used as herbicide.

3. A process of claim 1 in which process there is used 2-(5-chloroquinolin-8-yloxy)-acetic acid (1-methylheptyl) ester as antidote and 2-[4-(5-chloro-3-fluoropyridin-2-yloxy)phenoxy]-propionic acid propargyl ester as herbicide.

4. A process of claim 1 in which process there is used 2-(5-chloroquinolin-8-yloxy)-acetic acid (1-methylhexyl)ester as antidote and 2-[4-(5-chloro-3-fluoropyridin-2-yloxy)-phenoxy]propionic acid propargyl ester as herbicide.

5. A herbicidal composition which contains an effective amount of a herbicide of formula II

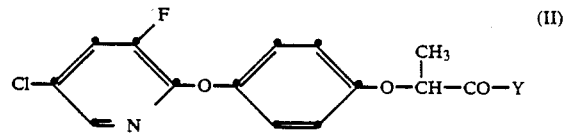

wherein
Y is $-OR^{18}$ and
$R^{18}$ is $C_3-C_9$ alkynyl and and effective amount of an antidote of formula I

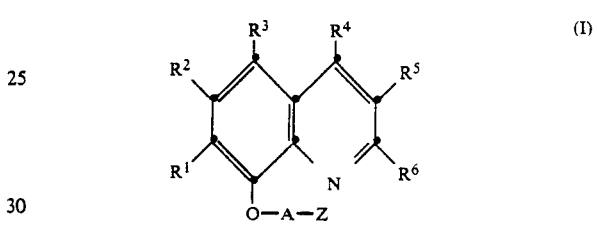

wherein $R^1$, $R^2$, $R^4$, $R^5$ and $R^6$ are hydrogen,
$R^3$ is hydrogen or chlorine,
A is $-CH_1-$,
Z is $COOR^{12}$ and
$R^{12}$ is an alkyl group of 4 to 11 carbon atoms and a carrier therefor.

6. A herbicidal composition of claim 5 which contains as herbicide 2-[4-(5-chloro-3-fluoro-pyridin-2-yl-oxy)-phenoxy]-propionic acid propargylester.

7. A herbicidal composition of claim 5 which contains 2-(5-chloroquinolin-8-yloxy)-acetic acid (1-methylheptyl) ester as antidote and 2-[4-(5-chloro-3-fluoropyridin-2-yl-oxy)phenoxy]-propionic acid propargyl ester as herbicide.

8. A herbicidal composition of claim 5 which contains 2-(5-chloroquinolin-8-yloxy)-acetic acid (1-methylhexyl) ester as antidote and 2-[4-(5-chloro-3-fluoropyridin-2-yloxy)phenoxy]propionic acid propargyl ester as herbicide.

* * * * *